(12) United States Patent
Caputo et al.

(10) Patent No.: US 8,624,035 B2
(45) Date of Patent: Jan. 7, 2014

(54) FUNCTIONALIZED CYANINE HAVING A SILANE LINKER ARM, A METHOD OF PREPARING THEREOF AND USES THEREOF

(75) Inventors: Giuseppe Caputo, Turin (IT); Ivana Miletto, Carmagnola (IT); Chiara Alessandra Bertolino, Cuorgne' (IT); Gianmario Martra, Bussoleno (IT); Salvatore Coluccia, Turin (IT)

(73) Assignee: Universita' Degli Studi di Torino, Turin (IT)

( * ) Notice: Subject to any disclaimer, the term of this patent is extended or adjusted under 35 U.S.C. 154(b) by 271 days.

(21) Appl. No.: 13/125,516

(22) PCT Filed: Oct. 21, 2009

(86) PCT No.: PCT/IB2009/054636
§ 371 (c)(1),
(2), (4) Date: Apr. 21, 2011

(87) PCT Pub. No.: WO2010/046856
PCT Pub. Date: Apr. 29, 2010

(65) Prior Publication Data
US 2011/0201784 A1    Aug. 18, 2011

(30) Foreign Application Priority Data
Oct. 22, 2008  (IT) .............. TO2008A0770

(51) Int. Cl.
C07F 7/02    (2006.01)
C07F 5/02    (2006.01)

(52) U.S. Cl.
USPC .............. 548/110; 548/406; 546/14

(58) Field of Classification Search
None
See application file for complete search history.

(56) References Cited

U.S. PATENT DOCUMENTS

2008/0095699 A1    4/2008    Zheng et al.

FOREIGN PATENT DOCUMENTS

| EP | 0 786 692 A1 | 7/1997 |
|---|---|---|
| EP | 0 822 447 A1 | 2/1998 |
| JP | 11-072862 A | 3/1999 |
| WO | WO 2006/076636 A | 7/2006 |
| WO | WO 2007/021946 A2 | 2/2007 |

OTHER PUBLICATIONS

Adriaensen, L. et al. "Matrix-enhanced secondary ion mass spectrometry: the influence of MALDI matrices on molecular ion yields of thin organic films", Rapid Communications in Mass Spectrometry, vol. 19, No. 8, Mar. 14, 2005, pp. 1017-1024.

Bringley, J. et al. "Silica nanoparticles encapsulating near-infrared emissive cyanine dyes", Journal of Colloid and Interface Science, Academic Press, vol. 320, No. 1, Sep. 7, 2007, pp. 132-139.

Wang, L. et al. "Watching Silica Nanoparticles Glow in the Biological World", Analytical Chemistry, vol. 78, No. 3, Feb. 1, 2006, pp. 646-654.

Mori, T. et al. "Preparation of a Water-Resistant Siliceous MCM-41 Sample, through Improvement of Crystallinity, and Its Prominent Adsorption Features", Langmuir, vol. 18, 2002, pp. 1595-1603.

*Primary Examiner* — Nyeemah A Grazier
(74) *Attorney, Agent, or Firm* — Merchant & Gould P.C.

(57) ABSTRACT

A silane-modified cyanine of Formula (I) includes the valence tautomers thereof: wherein $R_1$ is a linear, saturated or unsaturated alkyl chain, having 1 to 30 carbon atoms, wherein one or more carbon atoms are optionally substituted by a 4-, 5- or 6-membered aromatic or non aromatic cyclic grouping of carbon atoms; $R_8$ and $R_9$ are independently selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I, Formula (II), Formula (III), —$N(CH_3)_2$, Formula (IV), Formula (V), methyl, ethyl, propyl, isopropyl. The synthesis method and the use as a fluorescent marker are for inorganic solid supports, for example silica nanoparticles, and/or for biomolecules such as peptides, antibodies, DNA, RNA, etc.

16 Claims, 1 Drawing Sheet

Figure 1:
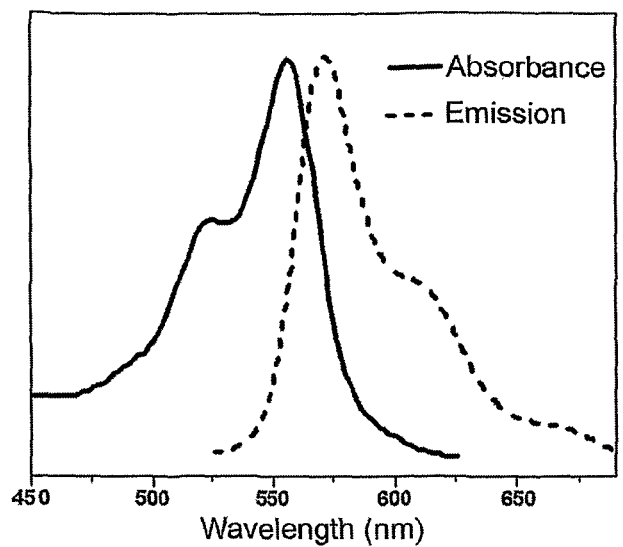

FUNCTIONALIZED CYANINE HAVING A SILANE LINKER ARM, A METHOD OF PREPARING THEREOF AND USES THEREOF

This application is a National Stage Application of PCT/IB2009/054636, filed 21 Oct. 2009, which claims benefit of Serial No. TO2008A000770, filed 22 Oct. 2008 in Italy and which applications are incorporated herein by reference. To the extent appropriate, a claim of priority is made to each of the above disclosed applications.

BACKGROUND OF THE INVENTION

The present invention relates to cyanine fluorescent dyes which are functionalized with silanes, their synthesis and their use in the manufacture of fluorescent solid supports, for example fluorescent surfaces or (nano)particles, in the bioconjugation and fluorescent labelling of biomolecules, such as for example nucleosides, nucleotides, nucleic acids (DNA, RNA or PNA), antibodies, proteins and peptides, as well as their use for immobilizing biomolecules on solid supports.

The fluorescent labelling technology is widely used in molecular biology, genomics, proteomics, analytical chemistry, since it is suitable to carry out highly sensitive and specifc tests, efficiently competing with techniques such as radioactive and enzymatic labelling.

DNA probes labelled with fluorescent moieties were shown to be valuable reagents for the separation and analysis of molecules. Specific applications of such fluorescent probes include for example automatic sequencing and DNA mapping; the identification of the concentration of a chemical species capable of binding a second chemical species (for example DNA hybridisation reactions in techniques such as real time PCR, in situ hybridization and molecular recognition with molecular beacons); the localization of biomolecules within cells, tissues or insoluble supports by techniques such as fluorescent staining.

Also fluorescent labelled proteins are very powerful analytical tools which are employed in techniques such as fluorescence microscopy, fluorescent immunoassays, protein chips, cytofluorimetry and laser induced fluorescence capillary electrophoresis.

Among fluorescent dyes, cyanines are widely used as biomolecule labels in several bioanalytical techniques, thanks to their physico-chemical properties such as the high extintion coefficient, the high quantum yield, the independence from pH, the low molecular weight and the possibility to carry out multiple assays with a plurality of fluorophores emitting at different wavelengths. The cyanines are also suitable for use as quenchers if their chemical structure contains suitable groups such as nitro groups.

To be useful as a fluorescent label or quencher in bioconjugations, the cyanine should be provided with a suitable functionalized linker arm having a reactive group.

The research in this filed has therefore focused in the study of innovative functionalized arms, since the chemistry and the behaviour of such linker arms may remarkably affect the fluorescence of the whole molecule as well as other chemical and physical properties such as hydrophobicity/hydrophilicity, aggregation and fluorescence quenching due to intramolecular interactions.

In general, the fluorescent dye molecule may contain a plurality of functionalized linker arms, which are preferably different one from each other in order to avoid the problem of cross-linking between identical molecules, of reticulation, of unwanted reactions or of purification.

There are examples in the literature wherein fluorescent molecules belonging to the class of rhodamines and fluoresceines, as well as luminescent ruthenium complexes, are conjugated to organosilane compounds by coupling reactions that require the use of reactive esters, which are synthesized on the organosilane reagent or on the fluorophore.

However, the use of active esters and generally of active carboxylic groups has remarkable drawbacks, such as the poor stability over time and the difficulty of the synthesis. As a matter of fact, active esters are poorly stable molecules under non anhydrous conditions and are therefore very difficult to store. They are prone to degrade over time by hydrolization and the percentage of active product in a package decreases over time. Moreover, due to their poor stability, it is almost impossible to further store the unused product immediately after opening the package. In addition, the need to work always under perfectly anhydrous conditions makes the synthesis of such compounds particularly difficult and expensive, in that the purification must be performed with the use of anhydrous eluents, especially when the synthesis is conducted on an industrial scale rather than on a lab scale.

International patent application WO2007021946, pages 17-18, discloses the synthesis of cyanines containing a silane functional group by reacting a carboxyl functional group with aminopropyl triethoxysilane in anhydrous pyridine under nitrogen flux for several hours. The final product is treated in anhydrous ether before being purified by chromatography.

The drawbacks of this procedure are the high costs, the complexity and, above all, the need to employ anhydrous solvents. Moreover, the amide bond formed between the cyanine carboxylic acid and the aminopropyl triethoxysilane, or other amine-derivative of silane, is not stable. As a matter of fact, such an amide bond may undergo hydrolization in the aqueous acidic or alkaline environment formed by the conditions required for immobilization of fluorescent derivatives on solid supports, thereby leading again to the formation of the cyanine carboxylic acid and the amino-derivative of silane according to the following scheme:

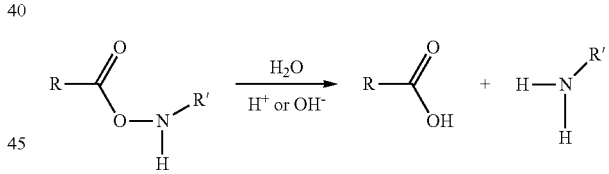

Similarly, the amide bonds of silane-functionalized cyanines formed by reacting an active ester of a cyanine, such as for example a succinimidyl ester, with an amino-derivative of a silane, may undergo hydrolization.

SUMMARY OF THE INVENTION

The object of the present invention is to provide a cyanine which contains a silane linker arm that does not possess the above-mentioned drawbacks of the prior art.

In particular, an object of the present invention is to provide a cyanine which contains a silane linker arm that does not require an expensive or difficult synthesis, particularly that does not require the use of anhydrous solvents.

Another object of the present invention is to provide a cyanine which contains a silane linker arm that is stable and is not readily hydrolysable.

A further object of the present invention is to provide a cyanine which contains a silane linker arm that is capable of being conjugated with a solid support suitable for performing bioanalytical and diagnostic assays, wherein the conjugation of the cyanine with the support does not lead to a reduction in the fluorophore performance.

These and other objects are achieved by a cyanine modified with a silane linker arm having the general formula (I), including the valence tautomers thereof:

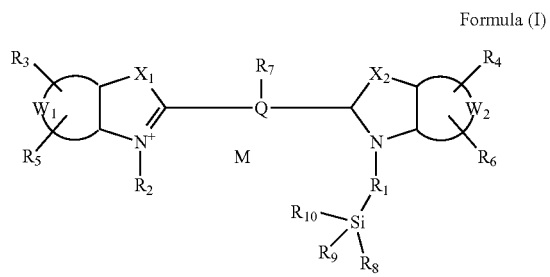

Formula (I)

wherein:

$R_1$ is a linear, saturated or unsaturated alkyl chain, having 1 to 30 carbon atoms, wherein one or more carbon atoms are optionally substituted by a 4-, 5- or 6-membered aromatic or non aromatic cyclic grouping of carbon atoms;

$R_8$ and $R_9$ are independently selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

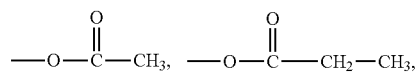

—$N(CH_3)_2$,

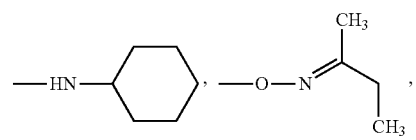

methyl, ethyl, propyl, isopropyl;

$R_{10}$ is selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

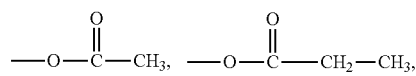

—$N(CH_3)_2$,

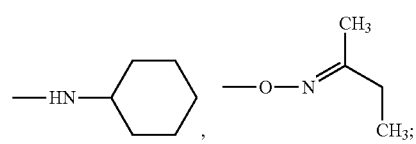

$W_1$ and $W_2$ are independently selected from a benzene ring and a naphthalene ring, in which one or more carbon atoms are optionally substituted by one or more heteroatoms selected from oxygen, sulphur, selenium and nitrogen, or one of $W_1$ and $W_2$ is absent, or both of $W_1$ and $W_2$ are absent;

$X_1$ and $X_2$ are independently selected from the group consisting of —O—, —S—, —Se—, —N—, —$C(CH_3)_2$, —CH=CH—, —NH—, and

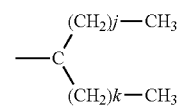

wherein j is an integer comprised between 1 and 20 and k is an integer comprised between 1 and 20;

$R_2$ is selected from the group consisting of hydrogen, —$CH_3$, and —$R_{11}$—$Y_1$, wherein $R_{11}$ is a linear, saturated or unsaturated alkyl chain, having 2 to 30 carbon atoms, wherein one or more carbon atoms are each substituted by a component independently selected from an oxygen atom, a sulphur atom, a —NH— group, a —CONH— group or a 4, 5 or 6-membered aromatic or non aromatic cyclic grouping of carbon atoms, wherein one or more carbon atoms are each optionally substituted by a heteroatom independently selected from oxygen, sulfur, nitrogen and selenium, and wherein $Y_1$ is selected from the group consisting of hydrogen, methyl, carboxyl, carbonyl, amino, sulphydryl, thiocyanate, isothiocyanate, isocyanate, maleimide, hydroxyl, phosphoramidite, glycidyl, imidazolyl, carbamoyl, anhydride, bromoacetamido, chloroacetamido, iodoacetamido, sulphonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, azide, 3-(2-pyridyldithio)-propionamide, glyoxal, aldehyde, nitrophenyl, dinitrophenyl, trinitrophenyl, $SO_3H$, $SO_3$—, —C≡CH and

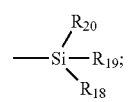

wherein $R_{18}$, $R_{19}$ are independently selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

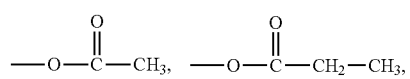

—$N(CH_3)_2$,

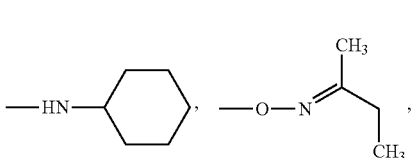

methyl, ethyl, propyl, isopropyl; and $R_{20}$ is selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

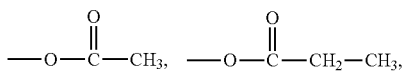

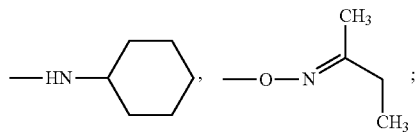

$R_3$, $R_4$, $R_5$ and $R_6$ are independently selected from the group consisting of hydrogen, —$CH_3$, —COOH, —OH, —$NO_2$, —$OCH_3$, —$SO_3H$, —$SO_3^-$, —Cl, —Br, —I, —O—($CH_2$—$CH_2$—$O)_n$—$CH_3$ wherein n is an integer comprised between 1 and 100, and —$R_{21}$—$Y_2$, wherein $R_{21}$ is a linear, saturated or unsaturated alkyl chain having 2 to 30 carbon atoms, wherein one or more carbon atoms are each optionally substituted by a component independently selected from an oxygen atom, a sulphur atom, an —NH— group, —CONH group or a 4-, 5- or 6-membered aromatic or non aromatic cyclic grouping of carbon atoms, wherein one or more carbon atoms are each optionally substituted by a heteroatom independently selected from oxygen, sulfur, nitrogen and selenium, and wherein $Y_2$ is selected from the group consisting of hydrogen, methyl, carboxyl, carbonyl, amino, sulphydryl, thiocyanate, isothiocyanate, isocyanate, maleimide, hydroxyl, phosphoramidite, glycidyl, imidazolyl, carbamoyl, anhydride, bromoacetamido, chloroacetamido, iodoacetamido, sulphonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, azide, 3-(2-pyridyldithio)-propionamide, glyoxal, aldehyde, nitrophenyl, dinitrophenyl, trinitrophenyl, $SO_3H$, $SO_3$—, and

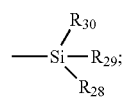

wherein $R_{28}$, $R_{29}$ are independently selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

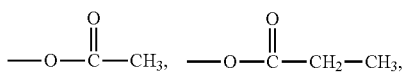

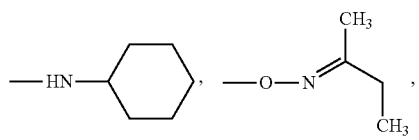

methyl, ethyl, propyl, isopropyl; and $R_{30}$ is selected from the group consisting of —$OCH_3$, —$OCH_2CH_3$, —$OCH_2CH_2CH_3$, —$OCH(CH_3)_2$, —$OCH_2CH_2OCH_3$—Cl, —Br, —I,

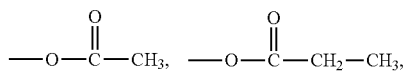

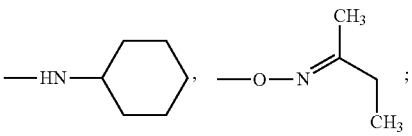

M is a counterion; and

Q is a polymethinic chain selected from the group consisting of:

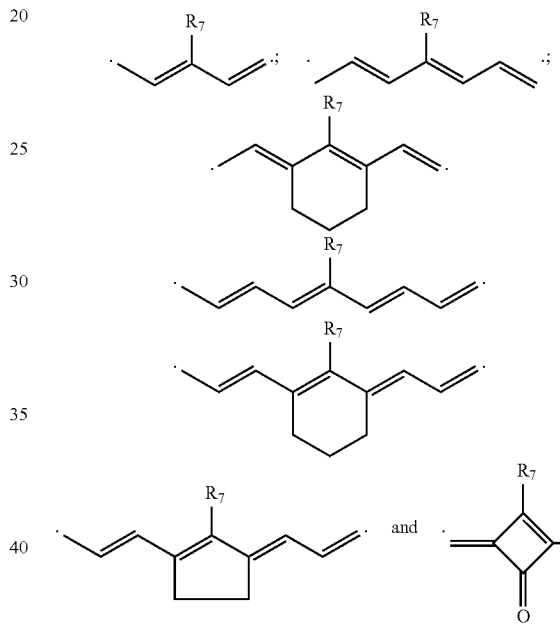

wherein $R_7$ is selected from the group consisting of hydrogen, halogen (for example fluorine, chlorine, bromide or iodine), =O, phenoxy, thiophenoxy, anilino, cyclohexylamino, pyridine, —$R_{31}$—$Y_3$, —O—$R_{31}$—$Y_3$, —S—$R_{31}$—$Y_3$, —NH—$R_{31}$—$Y_3$ and aryl optionally substituted with one or more substituents independently selected from the group consisting of —$SO_3H$, —$SO_3^-$, carboxyl (—COOH), amino (—$NH_2$), carbonyl (—CHO), thiocyanate (—SCN), isothiocyanate (—CNS), epoxy and —COZ wherein Z represents a leaving group, wherein $R_{31}$ has the same meanings as $R_{11}$ and $Y_3$ has the same meanings as $Y_1$.

Suitable leaving groups Z are for example —Cl, —Br, —I, —OH, —$OR_{15}$ or —$OCOR_{15}$, wherein $R_{15}$ is linear or branched lower $C_1$-$C_4$ alkyl (for example methyl, ethyl, t-butyl or i-propyl), —O—CO—Ar, wherein Ar is optionally substituted aryl, —O—CO-Het, wherein Het is selected from succinimide, sulfosuccinimide, phthalimide and naphthalimide, —$NR_{22}R_{33}$, wherein $R_{22}$ and $R_{33}$ are each independently linear or branched $C_1$-$C_{10}$ alkyl.

The expression "optionally substituted carbon atom" means that such a carbon atom in the linear alkyl chain or in the cyclic grouping of atoms may be replaced by one of the mentioned components or heteroatoms.

The cyanine of the present invention, which is modified with a silane linker arm, and which may also be designated as "silane-containing cyanine", allows to manufacture fluorescent solid supports such as fluorescent surfaces or nanoparticles in which the fluorescent dye is homogeneously dispersed, which leads to a remarkable signal enhancement and to the increase of the fluorophore performance, in terms of both photoluminescence yield and photo stability.

With the silane-containing cyanine of the present invention it is possible to manufacture nanometric devices that are capable of remarkably enhancing the signal. Furthermore, the silane-containing cyanine of the present invention allows to obtain fluorescent nanoparticles that are capable of emitting at different wavelengths and are capable of being conjugated with biomolecules, such as for example nucleosides, nucleotides, nucleic acids, antibodies and proteins, useful for performing bioanalytical and diagnostic assays and for molecular imaging.

Preferred examples of silane-containing cyanines that fall within the scope of the present invention are as follows:

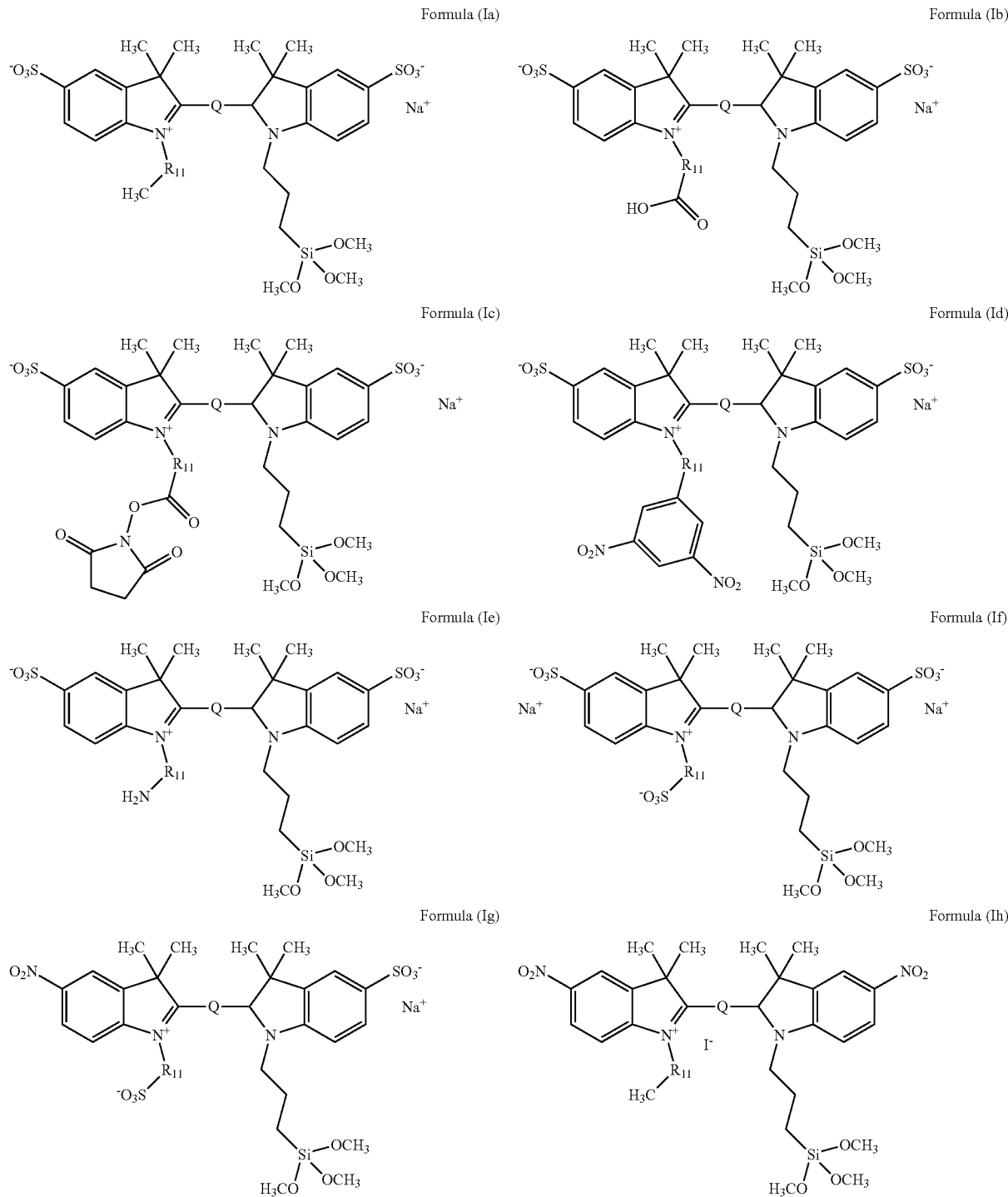

-continued
Formula (Ii)
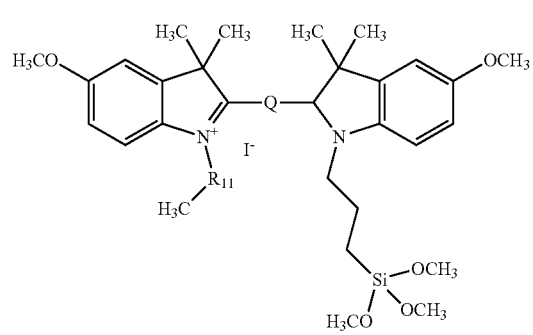
Formula (Il)
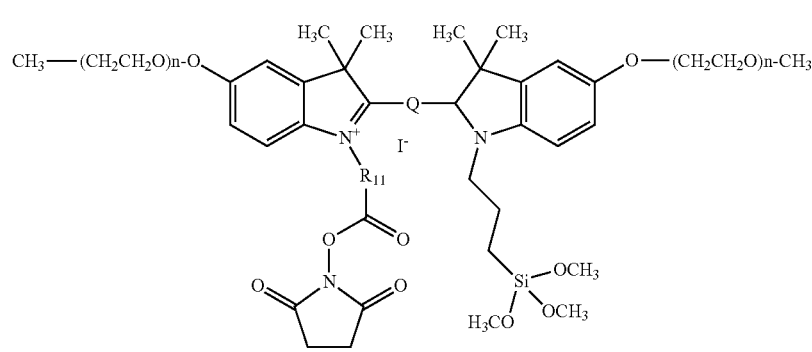
Formula (Im)
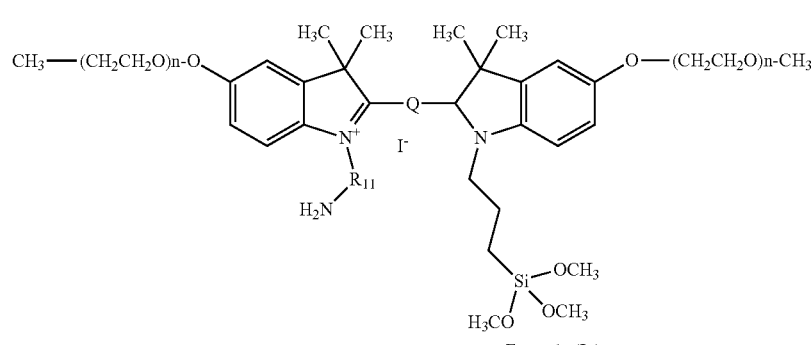
Formula (In)
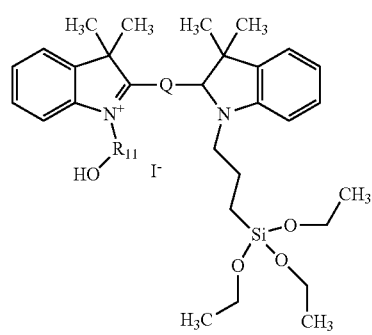
Formula (Io)
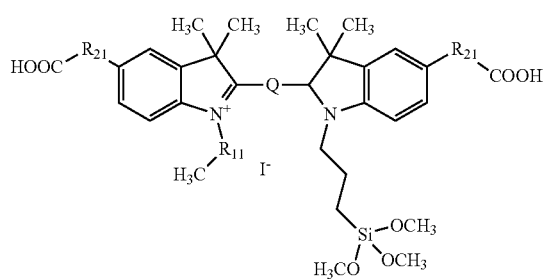
Formula (Ip)
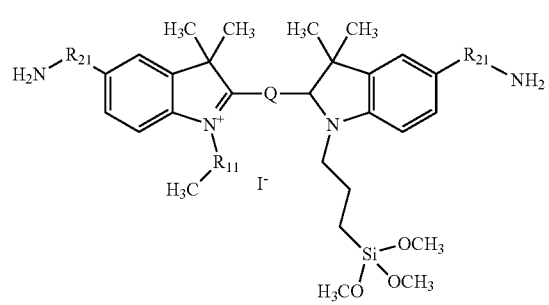
Formula (Iq)
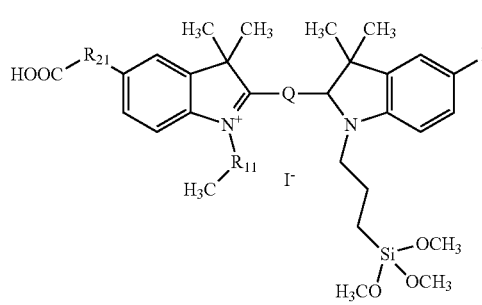

Formula (Ir)

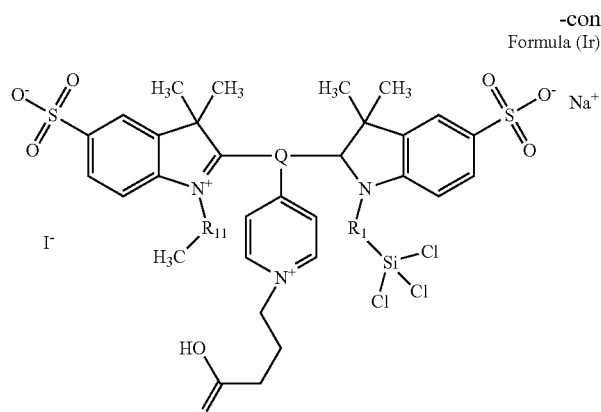

Formula (Is)

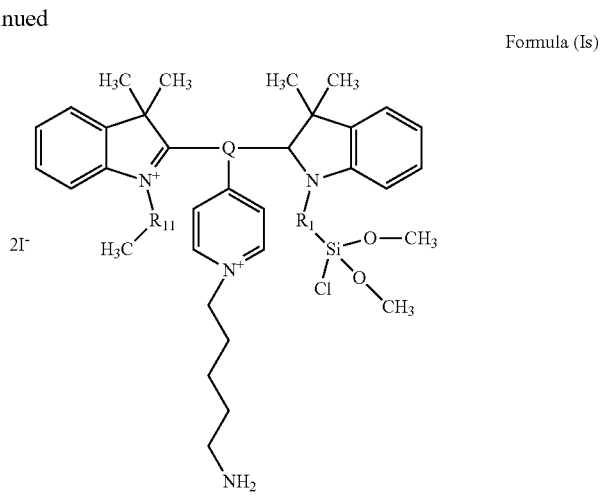

Formula I(t)

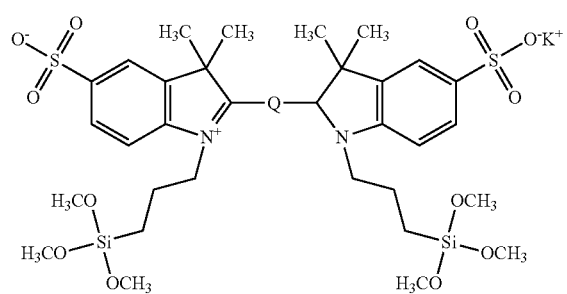

Formula I(u)

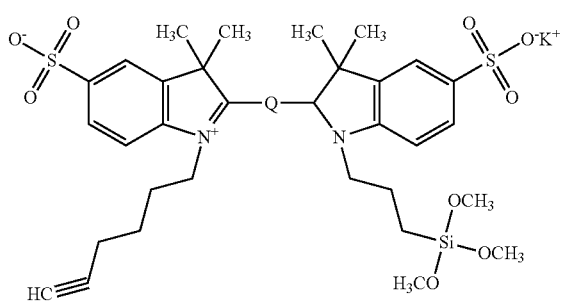

The silane-containing cyanines of formula (I) are synthesized according to a reaction scheme comprising the following steps:

1. synthesis of a quaternary ammonium salt functionalized with a silane (A),
2. synthesis of a second quaternary ammonium salt (B),
3. synthesis of the hemicyanine, and
4. synthesis of the cyanine.

Step 1 is carried out by reacting, in a suitable solvent such as sulfolane, acetonitrile or N,N-dimethylformamide, a nitrogen containing heterocyclic system ($A_1$) with a terminal silane-containing molecule ($A_2$) to provide the silane-functionalized quaternary ammonium salt (A):

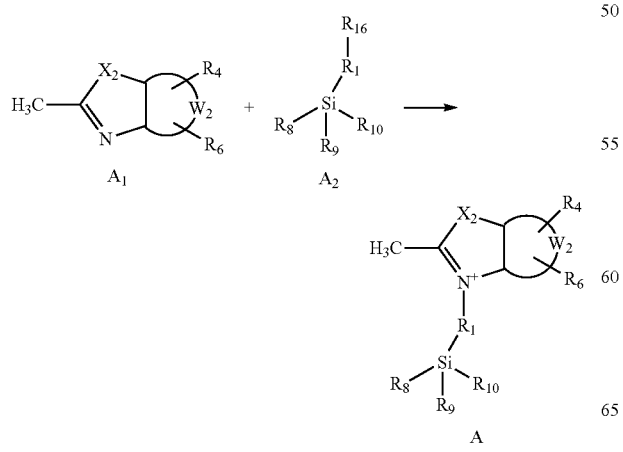

wherein $X_2$, $R_1$, $R_4$, $R_6$ and $W_2$, $R_8$, $R_9$, $R_{10}$ are as defined in formula (I); $R_{16}$ is selected from the group consisting of iodine, chlorine, bromine, OH, sulphate and tosylate.

Step 2 consists of the synthesis of a second quaternary ammonium salt (B) starting from a second nitrogen-containing heterocyclic system ($B_1$) and an alkylating molecule $R_2$—$R_{16}$ ($B_2$) according to the following scheme:

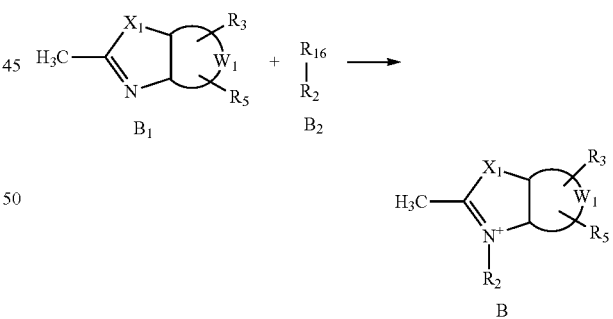

wherein $X_1$, $R_2$, $R_3$, $R_5$ and $W_1$ are as defined in formula (I) and $R_{16}$ is selected from the group consisting of iodine, chlorine, bromine, OH, sulphate and tosylate.

Step 3 can be carried out either on the silane-containing quaternary ammonium salt (A) synthesised in step 1 or on the quaternary ammonium salt (B) synthesised in step 2.

This step consists in the reaction between A or B and a compound capable of reacting with the heterocyclic quaternary ammonium salt thereby providing the polymethinic chain:

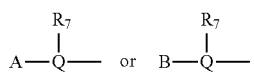

Nonlimiting examples of such compounds are triethylortoformiate, N,N-diphenylformamide, malonaldehyde dianylide, pyridylmalonaldehyde, trimethoxypropene, pentamidinium chloride, chloromalonaldehyde dianylide and squaric acid. Step 3 provides an intermediate designated as hemicyanine. By way of example, the structural formula of the hemicyanine obtained by reacting the intermediate A with malonaldehyde dianylide is provided herein below:

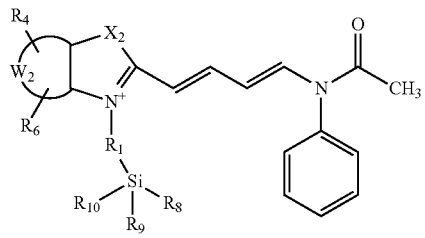

Step 4 is carried out by reacting the hemicyanine obtained in step 3 with the heterocyclic quaternary ammonium salt A or B not used in the previous step. A silane-containing cyanine of formula (I) is obtained.

In all the steps illustrated above, the reaction conditions depend on the reagents employed in the various passages and on the desired final product.

Due to the presence of at least one linker arm functionalized with a silane group, the silane-containing cyanines of formula (I) are capable of reacting with hydroxyl or silanol (Si—OH) groups exposed on a solid support such as for example a surface or a particle of any size and geometrical shape. Such properties render the silane-containing cyanines of formula (I) suitable for use in preparing fluorescent solid supports, such as for example fluorescent nanoparticles, as well as for the functionalization of surfaces with biomolecules of analytical and diagnostic interest, for the manufacture of devices suitable for optical visualization of events and reactions which take place inside the cells, for the visualization of receptors on cells or tissues, for the manufacture of tools for in vivo molecular imaging.

Thus, a silane-containing cyanine of formula (I) conjugated, through a silane linker arm, to a solid support containing exposed hydroxyls, also falls within the scope of the present invention.

DETAILED DESCRIPTION OF THE PREFERRED EMBODIMENT

A preferred embodiment of the silane-containing cyanine conjugated with a solid support is represented by the following general formula (II):

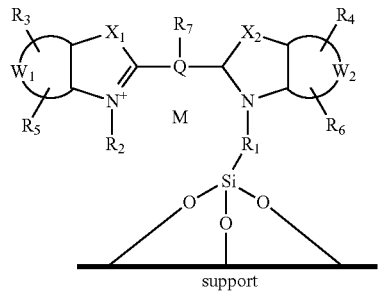

Formula (II)

wherein $R_1$, $R_2$, $R_3$, $R^4$, $R_5$, $R_6$, $R_7$, $X_1$, $X_2$, $W_1$, $W_2$, M and Q are as defined in connection with formula (I).

Another preferred embodiment of the silane-containing cyanine conjugated with a solid support is represented by the following general formula (III):

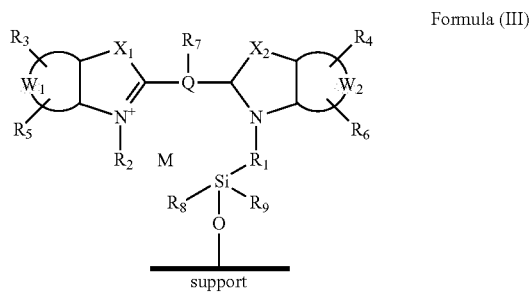

Formula (III)

wherein $R_1$, $R_2$, $R_3$, $R_4$, $R_5$, $R_6$, $R_7$, $X_1$, $X_2$, $W_1$, $W_2$, M and Q are as defined in connection with formula (I).

When the cyanine contains more than one silane linker arm (for example —$Si(R_{18})(R_{19})(R_{20})$ and/or —$Si(R_{28})(R_{29})(R_{30})$ in addition to —$Si(R_8)(R_9)(R_{10})$), it should be understood that the conjugation with the solid support can take place through any one of the silane linker arms or even through a plurality of silane linker arms.

The solid support containing exposed hydroxyls can be for example an amorphous silica (e.g. aerosil), a zeolite (e.g. ZSM-5, faujasite, zeolite-A, mordenite), a mesoporous silica (e.g. MCM-41, MCM-48, SBA-15, SBA-16), a metal, a metal chloride (e.g. $CuCl_2$, $Fe(Cl)_3$), a metal sulphate (e.g. $NaSO_4$, $Ce(SO_4)_2$), a metal oxide (e.g. magnetite, $Fe_3O_4$, $Fe_2O_3$, MgO, $TiO_2$, $Al_2O_3$, $ZrO_2$, $Y_2O_3$, $SnO_2$), a rare earth metal oxide (e.g. $CeO_2$, $Eu_2O_3$, $Gd_2O_3$), a transition metal oxide, a mixed oxide of two or more metals, a metal alloy, an inorganic semiconductor (e.g. CdS, CdSe, CdTe, ZnS, ZnSe, ZnTe, GaAs, InGaAs, InP, InAs, Ge, Si), diamond.

The support can be a flat surface or a particle of any geometrical shape and of any size, for example, a spherical or substantially spherical particle. The particle is preferably a nanoparticle, having at least one size lower than 500 nm. If the particle is spherical, the size lower than 500 nm is the particle diameter.

The silane-containing cyanine can be immobilized on an outer surface of the particle or it can be immobilized within the particle during the synthesis of the particle by mixing the silane-containing cyanine according to the present invention with the reagents that, by polymerization in a microemulsion, form a solid particle structure, for example according to the method disclosed in Wang et al. (Analytical Chemistry, 2006 (3), 646-654).

The conjugation reaction of the silane-containing cyanine on the solid support that contains exposed hydroxyls is carried out in a suitable anhydrous organic solvent, for example anhydrous N,N-dimethylformamide (DMF) or anhydrous toluene. The reaction is preferably carried out under reflux and in the dark for 12 to 18 hours. When the reaction time has elapsed, the functionalized support is removed from the reaction solvent, washed and subjected to thermal treatment, for example in an oven at a temperature of between 90 and 150° C. for 15-18 hours. Such a thermal treatment is essential for the completion of the condensation of the silane linker of the cyanine with the hydroxyls of the support.

A preferred embodiment of the invention is a silane-containing cyanine of formula (I) wherein at least one of $R_2$, $R_3$, $R_4$, $R_5$ and $R_6$ contains a reactive functional group different from a silane group. Such a second reactive functional group is preferably selected from carboxyl, amino, sulphydryl, tiocyanate maleimide, succinimidyl ester and hydrazine.

In this instance, the cyanine is a bifunctional or multifunctional molecule (depending on the total number of reactive functional groups it contains), which is advantageously capable of being immobilized onto solid supports having exposed hydroxyls groups and is simultaneously capable of being conjugated with a biomolecule such as a protein, a peptide, a nucleoside, a nucleotide, an oligonucleotide, a nucleic acid, a vitamin or an hormone.

A bifunctional silane-containing cyanine conjugated with both a solid support and a biomolecule is represented by the following general formula (IV):

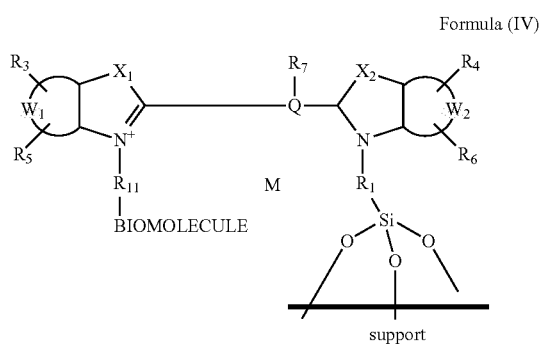

Formula (IV)

wherein $R_1$, $R_3$, $R_4$, $R_5$, $R_6$, $R_7$, $R_{11}$, $X_1$, $X_2$, $W_1$, $W_2$, M and Q are as defined in connection with formula (I).

Another embodiment of the bifunctional silane-containing cyanine conjugated with both a solid support and a biomolecule is represented by the following general formula (V):

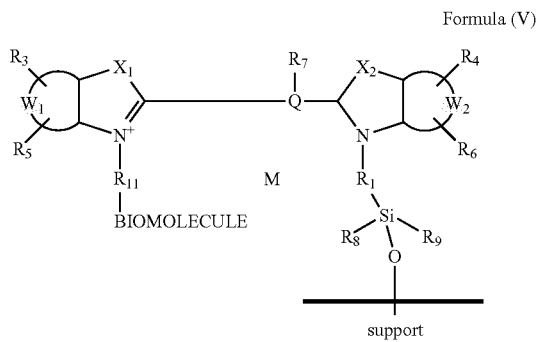

Formula (V)

wherein $R_1$, $R_3$, $R_4$, $R_5$, $R_6$, $R_7$, $R_{11}$, $X_1$, $X_2$, $W_1$, $W_2$, M and Q are as defined in connection with formula (I).

The bifunctional silane-containing cyanines of the invention are useful for preparing fluorescent oligonucleotides or proteins immobilized on the surface of nanoparticles, useful in molecular recognition assays with signal enhancement.

The following examples are provided by way of illustration only and should not be intended to limit the scope of the invention as defined in the appended claims.

EXAMPLE 1

Synthesis of 1-propyltrimethoxysilane-1'-propyltrimethoxysilane-3,3,3,3'-tetramethyl-5,5'-disulfonate-indomonocarbocyanine potassium salt (IRIS3 sulfo silane) (Compound 1)

a) Synthesis of N-propyltrimethoxysilane-2,3,3-trimethylindoleninium-5-sulfonate 2,3,3-trimethyl-3H-indolenine-5-sulfonate potassium salt (5 g; 0.02 mol) was dissolved in sulfolane and placed in a round bottom flask, heated in a oil bath at 100° C., equipped with a condenser. When the 2,3,3-trimethyl-3H-indolenine-5-sulfonate potassium salt was completely dissolved, 11.6 g (0.04 mol) of iodopropyltrimethoxysilane were added.

The reaction mixture was stirred at reflux (100° C.) for 20 hours. The reaction mixture was then cooled at r.t. and added dropwise to 800 ml of diethyl ether. The suspension obtained was filtered and the product recovered on a filter, washed with diethyl ether and dried in vacuum in a desiccator.

b) Synthesis of IRIS3 sulfo silane 2 g (4.5 mmol) of N-propyltrimethoxysilane-trimethylindoleninium-5-sulfonate, 0.98 g (10 mol) of potassium acetate, 0.882 g (4.5 mol) of N,N-diphenylphormamidine and 60 ml of acetic anhydride were placed in a 250 ml round bottom flask. The round bottom flask, equipped with a condenser, was placed into an oil bath preheated at 80° C. The reaction mixture was stirred at 80° C. for 15 hours, then the temperature was lowered at r.t. and the mixture was added dropwise to 600 ml of diethyl ether. The product was recovered by filtration on a sintered glass funnel, washed with diethyl ether and dried in vacuum in a desiccator. The product was purified by flash chromatography on reverse phase silica (RP-$C_{18}$), with gradient elution (dichloromethane/methanol from 98/2 to 40/60). Yield: 60%. The product has an absorption maximum centred at 556 nm (in water) and an emission maximum at 572 nm (in water).

FIG. 1 shows the absorption (-) and emission (- -) spectra of sulfo silane IRIS3 (Compound 1).

Compound 1

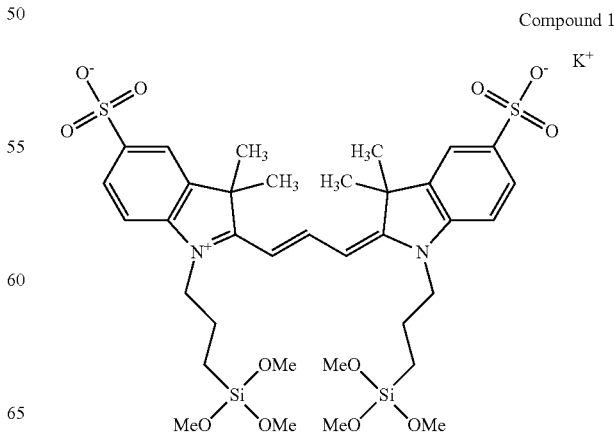

EXAMPLE 2

Synthesis of 1-(5-carboxypentyl)-1'-propyltrimethoxysilane-3,3,3',3'-tetramethyl-5,5'-disulfonate indodicarbocyanine potassium salt (Compound 2)

a) Synthesis of N-propyltrimethoxysilane-2,3,3-trimethylindoleninium-5-sulfonate 5 g (0.02 mol) of 2,3,3-trimethyl-3H-indolenine-5-sulfonate potassium salt were dissolved in the lower possible amount of sulfolane and placed in a round bottom flask in a oil bath, pre-heated at 130° C., equipped with a condenser. When the 2,3,3-trimethyl-3H-indolenine-5-sulfonate potassium salt was completely dissolved, 11.6 g (0.04 mol) of iodopropyl-trimethoxysilane were added.

The reaction mixture was stirred at reflux (100° C.) for 20 hours. The reaction mixture was then cooled at r.t. and added dropwise to 800 ml of diethyl ether. The suspension obtained was filtered and the product recovered on a sinterised glass filter, washed with diethyl ether and dried in vacuum in a desiccator.

b) Synthesis of N-(5-carboxypentyl)-2,3,3-trimethylindoleninium-5-sulfonate 5 g (0.02 mol) of 2,3,3-trimethyl-3H-indolenine-5-sulfonate potassium salt were dissolved in sulfolane and placed in a round bottom flask in a oil bath, pre-heated at 130° C., equipped with a condenser. When the 2,3,3-trimethyl-3H-indolenine-5-sulfonate potassium salt was completely dissolved, 9.6 g (0.04 mol) of iodohexanoic acid were added.

The reaction mixture was stirred at 130° C. for 18 hours. The reaction mixture was then cooled at r.t. and added dropwise to 800 ml of diethyl ether. The suspension obtained was filtered and the product recovered on a sintered glass filter, washed with diethyl ether and dried in vacuum in a desiccator.

c) Synthesis of 2-{(E)-2[acetyl(phenyl)amino]vinyl}-1-(5-carboxypentyl)-3,3-dimethyl-3H-indolium-5-sulfonate potassium salt (hemicyanine)

3.3 g (8.43 mmol) of N-(5-carboxypentyl)-2,3,3-trimethylindoleninium-5-sulfonate, 16.98 mmol of malonaldheyde dianylide hydrochloride, 6.0 ml of acetyl chloride and 60.0 ml of acetic anhydride were placed into a 250 ml round bottom flask. The mixture was heated and stirred at 120° C. for 90 min. The solution was cooled at r.t. and added dropwise to 500 ml of diethyl ether. The product was recovered on a sinterised glass filter, washed with di-ethyl ether and dried in vacuum in a desiccator.

d) Synthesis of 1-(5-carboxypentyl)-1'-propyltrimethoxysilane-3,3,3',3'-tetramethyl-5,5'-disulfonate indodicarbocyanine potassium salt 12.14 mmol of the hemicyanine synthesised in the previous step were placed in a 250 ml round bottom flask, with 5.35 g (12.14 mmol) of N-propyltrimethoxysilane-2,3,3-trimethylindoleninium-5-sulfonate, 10.80 ml of triethylamine and 100 ml of acetic anhydride. The reaction mixture was heated at 135° C. for 2 hours. The solution was then cooled to r.t. and added dropwise to 800 ml of diethyl ether. The product was recovered on a filter, washed with diethyl ether and dried in vacuum in a desiccator. The product was then purified by flash chromatography on reverse silica (RP-$C_{18}$) with gradient elution (dichloro-methane/methanol from 90/10 to 70/30).

Yield: 65%. The product has an absorption maximum centred at 655 nm (in water) and an emission maximum at 674 nm (in water).

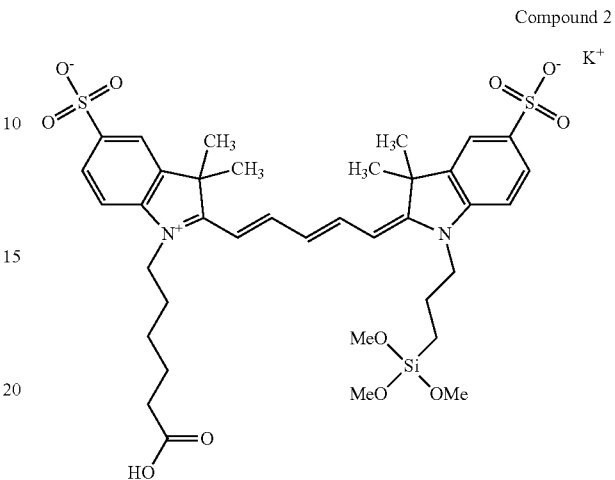

Compound 2

EXAMPLE 3

Use of Compound 1 for the Preparation of Photoactive Mesoporous Nanoparticles a) Preparation of the Mesoporous Material

The mesoporous material, of the MCM-41 type, was prepared according to the standard procedure disclosed in the literature (T. Mori, Y. Kuroda, Y. Yoshikawa, M. Nagao, S. Kittaka, Langmuir 2002, 18:1595), using cetyl trimethyl ammonium bromide (CTMAB) as the organic template.

b) Functionalization of the mesoporous material with Compound 1

The mesoporous material (hereafter MCM-41) was pre-treated by outgassing in at 150° C. for at least 4 hours, in order to remove physisorbed water. Then the material was impregnated with a solution of Compound 1 in anhydrous toluene (5 mg Compound 1 per 5 g of MCM-41). The suspension was stirred in Argon atmosphere for two hours. The material was then filtered and washed with solvents in order to remove dye molecules adsorbed on the outer surface of the mesoporous material. The product was then dried in oven at 150° C. (for the curing step, where the condensation of the silane termination of the fluorophore with the silanols of the MCM-41 occurs). After this stage, the fluorophore was covalently anchored inside the channels of the mesoporous material.

c) Reduction of the Fluorescent Mesoporous Material to Nanosize

The mesoporous material MCM-41, functionalized with Compound 1, was reduced to nanoparticles of homogeneous size (mean diameter 10 nm) by ultrasonication.

The nanoparticles thereby obtained were characterised by transmission electron microscopy and X-ray diffraction analysis; these measurements confirmed the maintenance of the mesoporous structure.

d) Surface Functionalization with Antibodies

Step 1: Coating of Nanoparticles with
3-aminopropyltriethoxysilane (APTES)

80 mg of MCM-41 nanoparticles were suspendend in anhydrous toluene; 400 µl of APTES were added to the suspension, which was stirred at r.t. for 4 hours. The material was then recovered by filtration, washed with toluene, then placed in an oven at 150° C. for the curing step.

Step 2: Exposure of Carboxyl Groups by Reaction of
Surface APTES with Succinic Anhydride The material obtained from step 1 of the present example was re-suspended in anhydrous toluene and stirred at 80° C. To this suspension, 0.8 g of succinic anhydride were added. The suspension was kept under stirring at 50° C. for 2 hours, then the solid was recovered through filtration and washed with toluene.

Step 3: Antibody Immobilization

The material obtained from step 2 of the present example was suspended in PBS buffer (0.1M pH 7.4) and stirred at r.t. EDC and subsequently 1 mg of antibody were then added to the solution. The reaction was carried out under stirring at r.t. for 2 hours. The material was recovered by centrifugation and washed with PBS buffer (0.1M pH 7.4) in order to remove unreacted antibodies.

EXAMPLE 4

Internalization and Citotoxicity Tests of Silica
Nanoparticles from Example 3

Functionalized nanoparticles prepared as reported in Example 3 were used for cellular tests in order to assess their internalization and citotoxicity. To that purpose, a comparison with commercial fluorescent particles (FITC loaded Latex beads) was carried out.

A human neuroblastoma cell line (SHSY5Y) was used. The preliminary tests carried out showed that silica nanoparticles were quickly uptaken into the cells, where they were retained for up to 96 hours, whilst Latex beads were almost completely expelled after 1 hour. Silica nanoparticles maintained a high luminescence for all the duration of the test.

EXAMPLE 5

Use of Silica Nanoparticle from Example 3 for
Visualization of Cellular Events

Functionalized nanoparticles prepared as reported in example 4 were used in cellular tests in order to monitor calcium regulated exocytosis. For endocytosis and exocytosis tests, RBL cells were used, that allow to study calcium regulated exocytosis of endosomes and lysosomes. Cells were incubated with a suspension of nanoparticles from example 3, in PBS buffer; after internalization, exocytosis was induced by administration of the calcium ionophore A23187. In order to better localize exocyted nanoparticles, a cell line stably transfected with chimeric protein cathepsin D-GFP (CD-GFP) was used, that allows to visualize endosomal and lysosomal compartments.

EXAMPLE 6

Use of 1-propyltrimethoxysilane-1'-propyltrimethoxysilane-3,3,3',3'-tetramethyl-5,5'-disulfonate-indomonocarbocyanine potassium salt (IRIS3 sulfo silane, Compound 1) for the Preparation of Fluorescent Silica Nanoparticles Compound 1 was used for the preparation of fluorescent silica nanoparticles in which compound 1 is covalently linked to the siliceous component, thanks to the presence of the silane groups. The preparation was carried out according to the following steps.

Step 1: preparation of the microemulsion according to a procedure reported in literature (Wang L. et al. Anal. Chem. 2006, 78 (3), 647-654). 75 ml of cyclohexane, 18 ml of n-hexanol, 5.4 ml of water and 17.7 ml of Triton X-100 were mixed.

Step 2: Addition of Compound 1 ($6 \times 10^{-7}$ mol) dissolved in DMF.

Step 3: Addition of the silica precursor TetraEthylOrthoSilicate (TEOS, 1 ml) and ammonia solution ($NH_4OH$ 30%, 0.7 ml) to start the hydrolysis reaction to silicic acid and condensation reaction of the silicic acid monomers. The reaction was carried out for 18 hours under stirring at r.t.

Step 4: Nanoparticles extraction from microemulsion and washing with ethanol and water.

Figure 2:
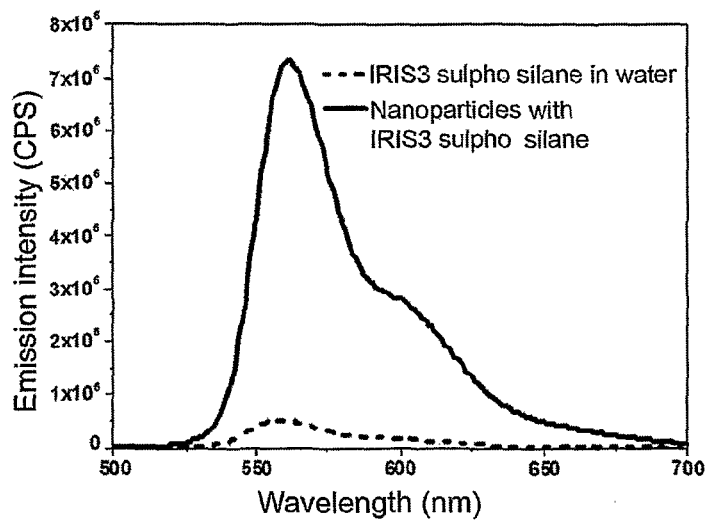
Figure 3:
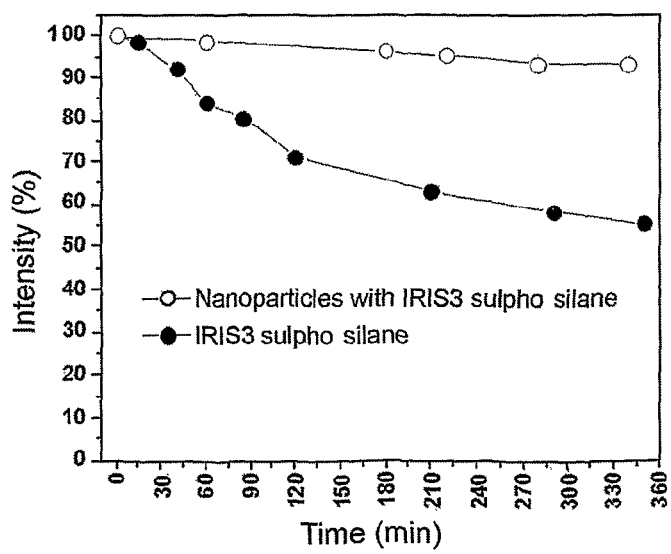

FIG. 2 shows the comparison between the fluorescence emission spectra of a solution of Compound 1, i.e. cyanine IRIS3 sulfo silane (- -) and an isoabsorbing suspension of silica nanoparticles containing the same cyanine IRIS3 sulfo silane (-). The emission of nanoparticles is 15-folds higher than the emission of the solution. Moreover, the photodegradation of fluorescent nanoparticles over time was compared to the photodegradation of the cyanine in solution. FIG. 3 shows the comparison graphs between the photodegradation of cyanine IRIS3 sulfo silane over time (Compound 1) in solution (●) and the same cyanine immobilized within a silica nanoparticle (○). The graph shows the percentage of emission, compared to time zero, under excitation with a laser light at 532 nm. It observed that the cyanine immobilized within the nanoparticle undergoes a 5% photodegradation after 350 minutes, whilst the cyanine dye in solution undergoes a 45% photodegradation within the same time.

EXAMPLE 7

Synthesis of the Conjugate Between 1-(5-carboxypentyl)-1'-propyltrimethoxysilane-3,3,3',3'-tetramethyl-5,5'-disulfonate indodicarbocyanine potassium Salt and the Protein Bovine Serum Albumin (BSA) (Compound 3)

a) Synthesis of the N-hydroxysuccinimidic Ester of
Compound 2

115 mg (0.14 mmol) of Compound 2 were dissolved in lower possible amount of anhydrous N,N-dimethylformamide and placed into a 25 ml round bottom flask previously dried and maintained under an argon atmosphere. 64 mg (0.56 mmol) of N-hydroxysuccinimide and 115 mg (0.56 mmol) of Diciclohexylcarbodiimide were also placed into the round bottom flask. The round bottom flask equipped with a condenser, was placed to react into an oil bath pre-heated at 80° C. The reaction mixture was maintained under stirring for 4 hours at 80° C. under Ar atmosphere, after which the mixture was cooled at r.t. and added dropwise to 1 l of diethyl ether.

The product was recovered by filtration on a sintered glass funnel, washed with ether and dried in vacuum in a desiccator.

b) Synthesis of the Conjugate with Bovine Serum Albumin 2 mg of Bovine Serum Albumin (BSA) were dissolved in PBS buffer (0.1M pH 7.4). 0.3 mg ($3 \times 10^{-7}$ mol) of N-hydroxysuccinimide ester of Compound 2, dissolved in 50 µl of N,N-dimethylformamide, were added to the solution, achieving a 10/1 fluorophore/protein molar ratio. The mixture was stirred at r.t. for 2 hours. After 2 hours, the conjugate was purified on Sephadex G25 resin and the fractions containing the conjugate were lyophilized and stored at −20° C. in a refrigerator.

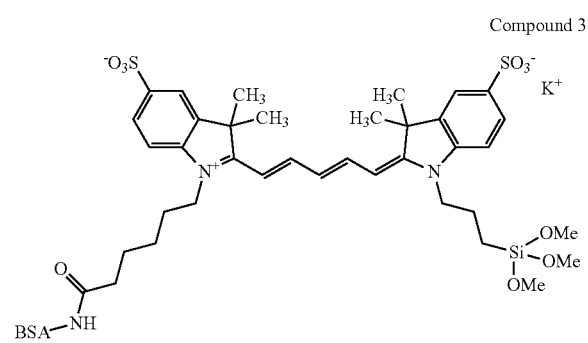

Compound 3

EXAMPLE 8

Immobilization of Compound 3 on the Surface of a Silica Nanoparticle a) Preparation of the Silica Nanoparticle Silica nanoparticles were prepared by following a microemulsion procedure reported in literature (Wang L. et al. Anal. Chem. 2006, 78 (3), 647-654), that lead to the formation of nanosphere of amorphous silica with a size of about 50 µm.

b) Immobilization of the N-hydroxysuccinimide Ester of Compound 2 on the Silica Nanoparticle N-hydroxysuccinimide ester of Compound 2, prepared as reported in item a) of example 3, was dissolved in anhydrous N,N-dimethylformamide and added to a suspension of the nanoparticles in anhydrous toluene. The suspension was stirred at 80° C. for 15 hours, then the material was recovered by filtration and washed with anhydrous toluene, then it was maintained in oven at between 80-120° C. for 15 hours.

c) Immobilization of the N-hydroxysuccinimide Ester of Compound 2 on the Silica Nanoparticle The nanoparticles functionalized as reported in the previous step were suspended in PBS buffer (0.1 M, pH 7.4). A BSA solution was added and the suspension was stirred for 2 hours at r.t., then the material was recovered by centrifugation and washed several times with buffer in order to remove the unreacted protein, if present.

EXAMPLE 9

Use of Compound 2 for the Preparation of Silicon Quantum Dots Functionalized with Fluorescent Molecules and Coated with a Silica Shell a) Preparation of Functionalized Silicon Quantum Dots Silicon quantum dots were prepared by electrochemical dissolution of porous silicon, and then functionalized with a convenient organic molecule that leads to the exposure of free amino groups on the surface.

b) Binding of Compound 2 on the Surface of Silicon Quantum Dots

Step 1: Synthesis of the N-hydroxysuccinimidic Ester of Compound 2

115 mg (0.14 mmol) of Compound 2 were dissolved in the lower possible amount of anhydrous N,N-dimethylformamide and placed into a 25 ml round bottom flask previously died and maintained under an Argon atmosphere. 64 mg (0.56 mmol) of N-hydroxysuccinimide and 115 mg (0.56 mmol) of Diciclohexylcarbodiimide were also placed into the round bottom flask. The round bottom flask, equipped with a condenser, was placed to react into an oil bath pre-heated at 80° C. The reaction mixture was carried out under stirring for 4 hours at 80° C. under an Ar atmosphere, after which the mixture was cooled at r.t. and added dropwise to 1 l of diethyl ether. The product was recovered by filtration on a sintered glass funnel, washed with ether and dried in vacuum in a desiccator.

Step 2: Immobilization of the N-hydroxysuccinimide Ester of Compound 2 on the Surface of Silicon Quantum Dots To a suspension of silicon quantum dots in anhydrous N,N-dimethylformamide, a variable amount of N-hydroxysuccinimide ester of Compound 2, depending on the density of amino groups on silicon quantum dots surface, was added. The suspension was stirred for 2 hours and the material was recovered by centrifugation and washed with adequate solvents in order to remove unreacted fluorophore.

c) Deposition of the External Silica Shell

The molecules of Compound 2 immobilized on the surface of silicon quantum dots can be exploited as anchoring moieties for the coating of quantum dots with different type of siliceous precursors (TEOS, TMOS, etc.), in an acidic or alkaline hydrolysis and condensation reaction, similar to that described in steps 3 and 4 of example 5.

The invention claimed is:

1. A cyanine functionalized with a silane linker arm of formula (I), or a valence tautomer thereof:

Formula (I)

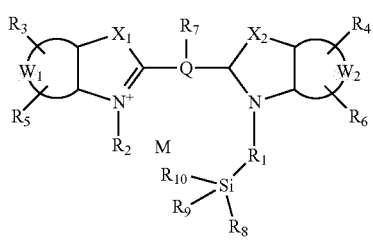

wherein:

$R_1$ is a linear, saturated or unsaturated alkyl chain, having 1 to 30 carbon atoms, wherein one or more carbon atoms are optionally substituted by a 4-, 5- or 6-membered aromatic or non aromatic cyclic grouping of carbon atoms;

$R_8$ and $R_9$ are independently selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

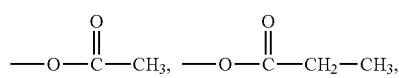

—$N(CH_3)_2$,

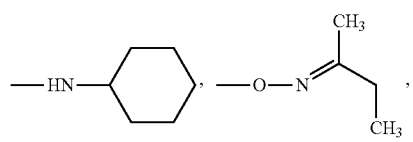

methyl, ethyl, propyl, and isopropyl;

$R_{10}$ is selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

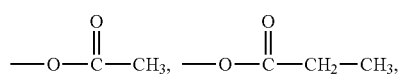

—$N(CH_3)_2$,

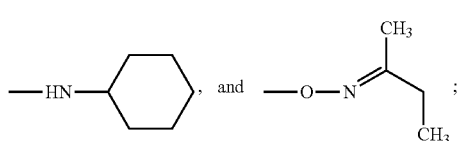

$W_1$ and $W_2$ are independently selected from a benzene ring or a naphthalene ring, in which one or more carbon atoms are optionally substituted by one or more heteroatoms selected from oxygen, sulfur, selenium and nitrogen, or one of $W_1$ and $W_2$ is absent, or both of $W_1$ and $W_2$ are absent;

$X_1$ and $X_2$ are independently selected from the group consisting of —O—, —S—, —Se—, —N—, —$C(CH_3)_2$, —CH=CH—, —NH—, and

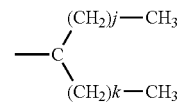

wherein j is an integer comprised between 1 and 20 and k is an integer comprised between 1 and 20;

$R_2$ is selected from the group consisting of hydrogen, —$CH_3$, and —$R_{11}$—$Y_1$, wherein $R_{11}$ is a linear, saturated or unsaturated alkyl chain, having 2 to 30 carbon atoms, wherein one or more carbon atoms are each substituted by a component independently selected from an oxygen atom, a sulfur atom, a —NH— group, a —CONH— group or a 4, 5 or 6-membered aromatic or non aromatic cyclic grouping of carbon atoms, wherein one or more carbon atoms are each optionally substituted by a heteroatom independently selected from oxygen, sulfur, nitrogen, or selenium, and wherein $Y_1$ is selected from the group consisting of hydrogen, methyl, carboxyl, carbonyl, amino, sulphydryl, thiocyanate, isothiocyanate, isocyanate, maleimide, hydroxyl, phosphoramidite, glycidyl, imidazolyl, carbamoyl, anhydride, bromoacetamido, chloroacetamido, iodoacetamido, sulphonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, azide, 3-(2-pyridyldithio)-propionamide, glyoxal, aldehyde, nitrophenyl, dinitrophenyl, trinitrophenyl, $SO_3H$, $SO_3^-$, —C≡CH and

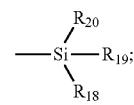

wherein $R_{18}$ and $R_{19}$ are independently selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

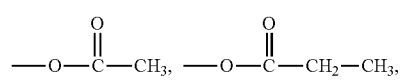

—$N(CH_3)_2$,

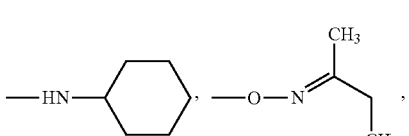

methyl, ethyl, propyl, and isopropyl;

$R_{20}$ is selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

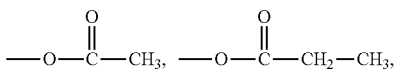

—N(CH$_3$)$_2$,

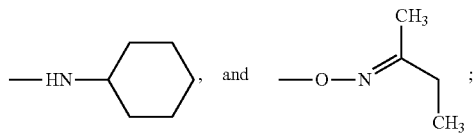

$R_3$, $R_4$, $R_5$ and $R_6$ are independently selected from the group consisting of hydrogen, —CH$_3$, —COOH, —OH, —NO$_2$, —OCH$_3$, —SO$_3$H, —SO$_3^-$, —Cl, —Br, —I, —O—(CH$_2$—CH$_2$—O)$_n$—CH$_3$ wherein n is an integer comprised between 1 and 100, and —R$_{21}$—Y$_2$, wherein R$_{21}$ is a linear, saturated or unsaturated alkyl chain having 2 to 30 carbon atoms, wherein one or more carbon atoms are each optionally substituted by a component independently selected from an oxygen atom, a sulfur atom, an —NH— group, —CONH group or a 4-, 5- or 6-membered aromatic or non aromatic cyclic grouping of carbon atoms, wherein one or more carbon atoms are each optionally substituted by a heteroatom independently selected from oxygen, sulfur, nitrogen, or selenium, and wherein Y$_2$ is selected from the group consisting of hydrogen, methyl, carboxyl, carbonyl, amino, sulphydryl, thiocyanate, isothiocyanate, isocyanate, maleimide, hydroxyl, phosphoramidite, glycidyl, imidazolyl, carbamoyl, anhydride, bromoacetamido, chloroacetamido, iodoacetamido, sulphonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, azide, 3-(2-pyridyldithio)-propionamide, glyoxal, aldehyde, nitrophenyl, dinitrophenyl, trinitrophenyl, —C≡CH, SO$_3$H, SO$_3^-$, and

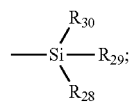

wherein R$_{28}$ and R$_{29}$ are independently selected from the group consisting of —OCH$_3$, —OCH$_2$CH$_3$, —OCH$_2$CH$_2$CH$_3$, —OCH(CH$_3$)$_2$, —OCH$_2$CH$_2$OCH$_3$, —Cl, —Br, —I,

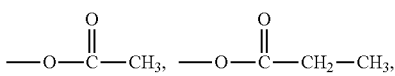

—N(CH$_3$)$_2$,

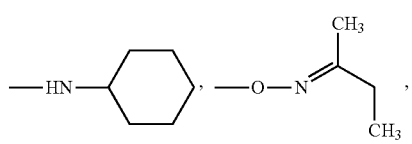

methyl, ethyl, propyl, and isopropyl;

R$_{30}$ is selected from the group consisting of —OCH$_3$, —OCH$_2$CH$_3$, —OCH$_2$CH$_2$CH$_3$, —OCH(CH$_3$)$_2$, —OCH$_2$CH$_2$OCH$_3$, —Cl, —Br, —I,

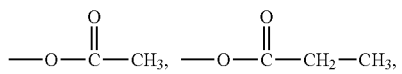

—N(CH$_3$)$_2$,

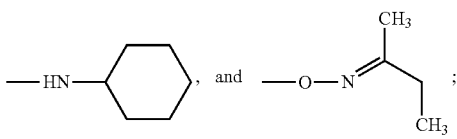

M is a counterion; and

Q is a polymethinic chain selected from the group consisting of:

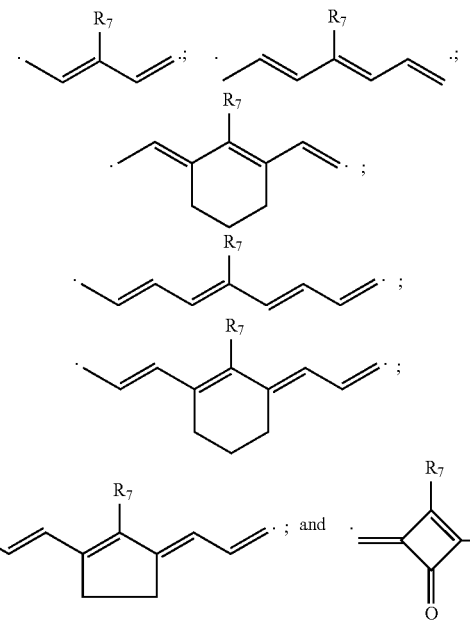

wherein R$_7$ is selected from the group consisting of hydrogen, halogen, =O, phenoxy, thiophenoxy, anilino, ciclohexylamino, piridine, —R$_{31}$—Y$_3$, —O—R$_{31}$—Y$_3$, —S—R$_{31}$—Y$_3$, —NH—R$_{31}$—Y$_3$ and aryl optionally substituted with one or more substituents independently selected from the group consisting of —SO$_3$H, —SO$_3^-$, carboxyl (—COOH), amino (—NH$_2$), carbonyl (—CHO), thiocyanate (—SCN), isothiocyanate (—CNS), epoxy and —COZ wherein Z represents a leaving group, wherein R$_{31}$ has the same meanings as R$_{11}$ and Y$_3$ has the same meanings as Y$_1$.

2. A cyanine according to claim 1, wherein the leaving group Z is selected from the group consisting of —Cl, —Br, —I, —OH, —OR$_{15}$ and —OCOR$_{15}$, wherein R$_{15}$ is linear or branched lower C$_1$-C$_4$ alkyl (for example methyl, ethyl, t-butyl or i-propyl), —O—CO—Ar, wherein Ar is optionally substituted aryl, —O—CO-Het, wherein Het is selected from succinimide, sulfosuccinimide, phthalimide; naphthalimide, or —NR$_{22}$R$_{33}$, wherein R$_{22}$ and R$_{33}$ are each independently linear or branched C$_1$-C$_{10}$ alkyl.

3. A cyanine according to claim 1, selected from the group consisting of:
Formula (Ia)
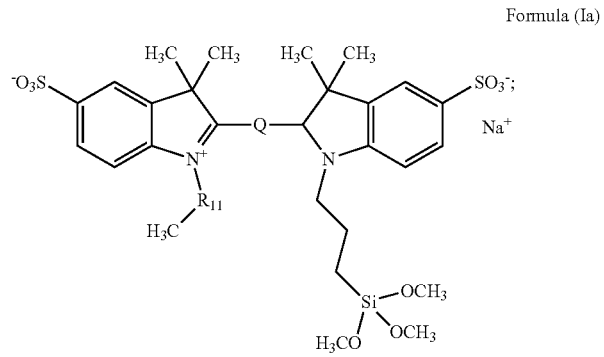
Formula (Ib)
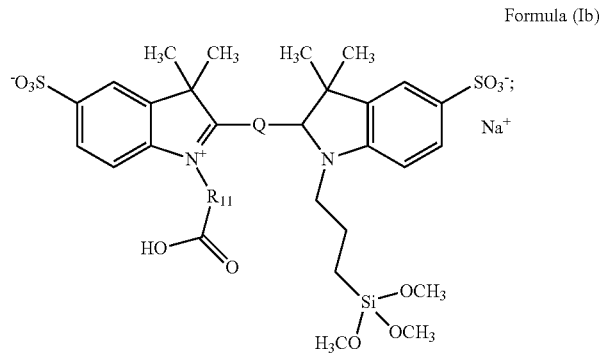
Formula (Ic)
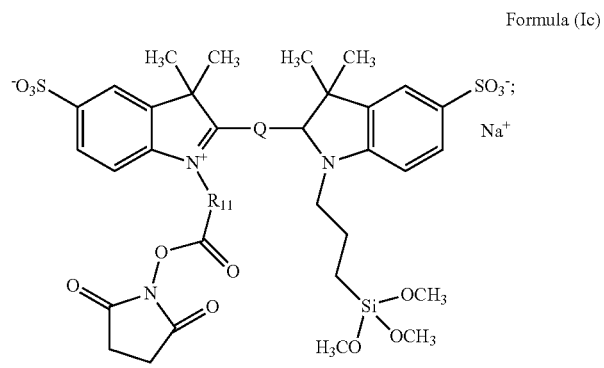
Formula (Id)
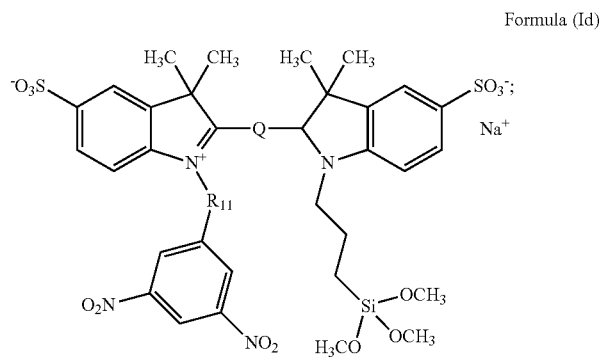
Formula (Ie)
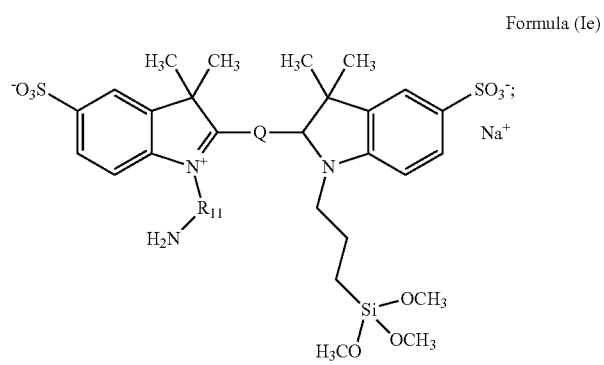
Formula (If)
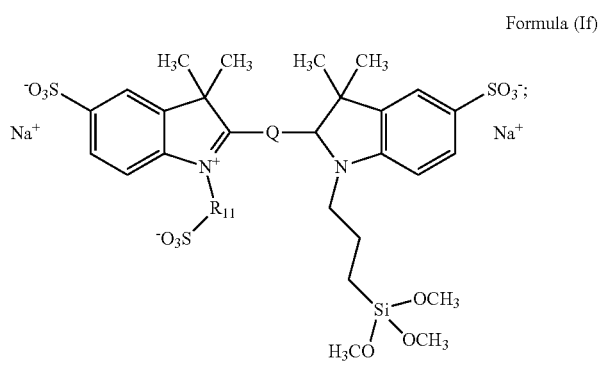
Formula (Ig)
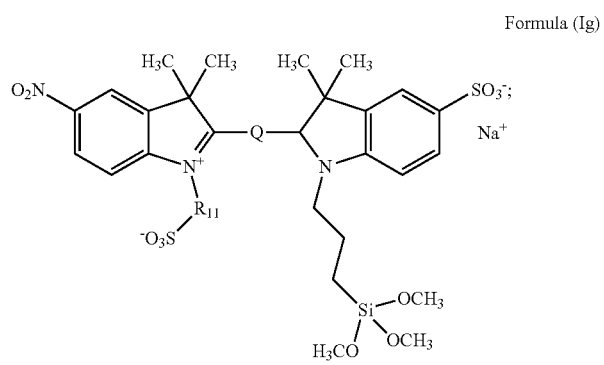
Formula (Ih)
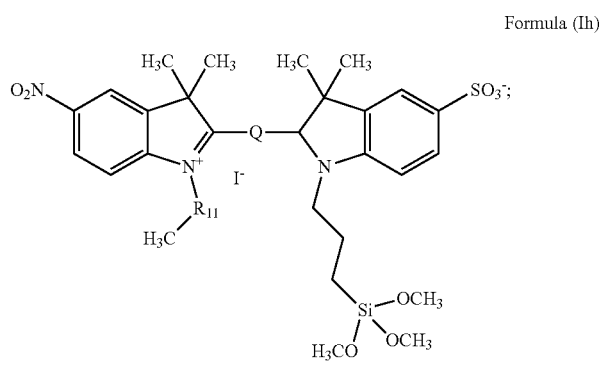

-continued
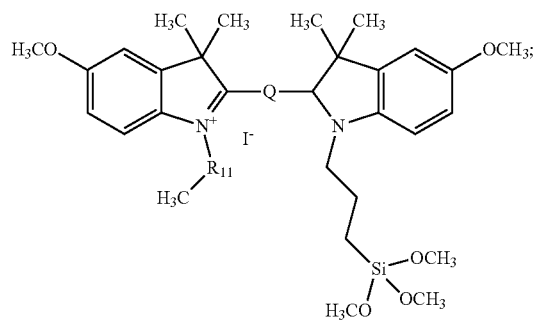
Formula (Ii)
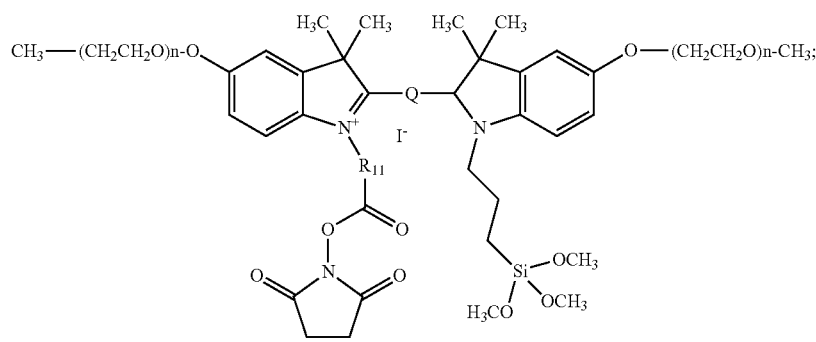
Formula (Il)
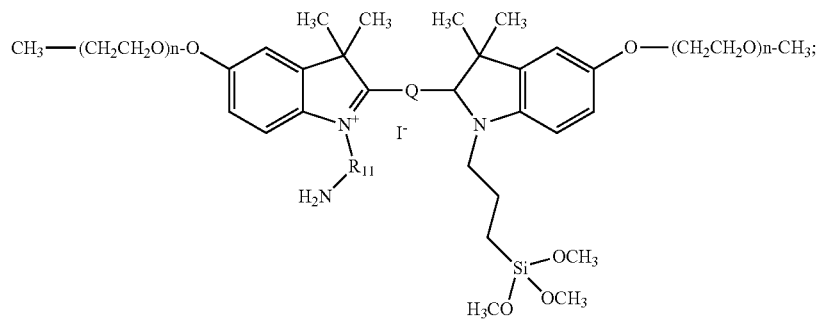
Formula (Im)
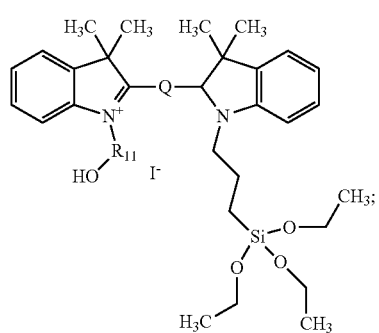
Formula (In)
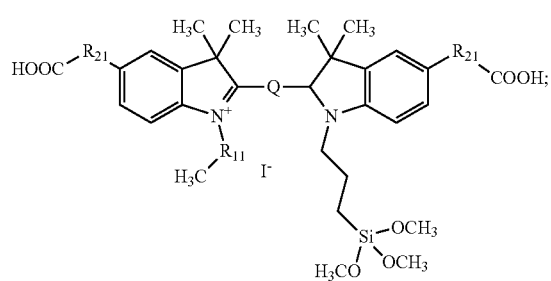
Formula (Io)
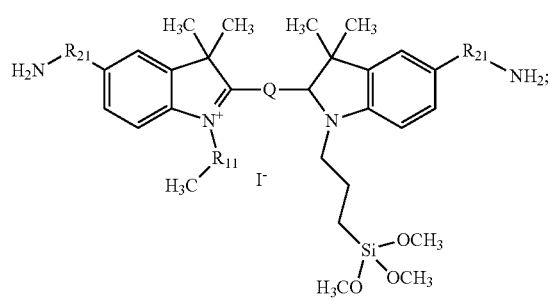
Formula (Ip)
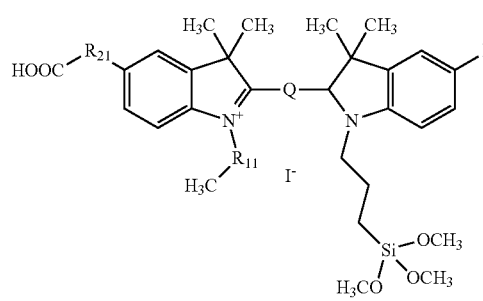
Formula (Iq)

-continued

Formula (Ir)
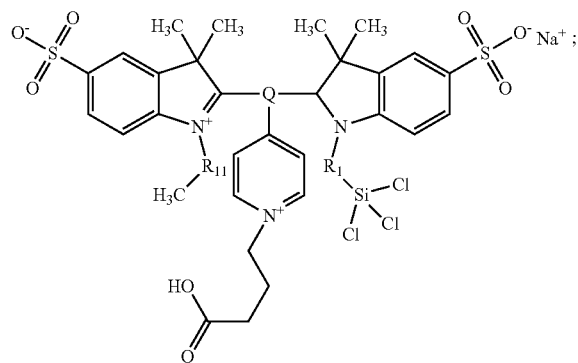

Formula (Is)
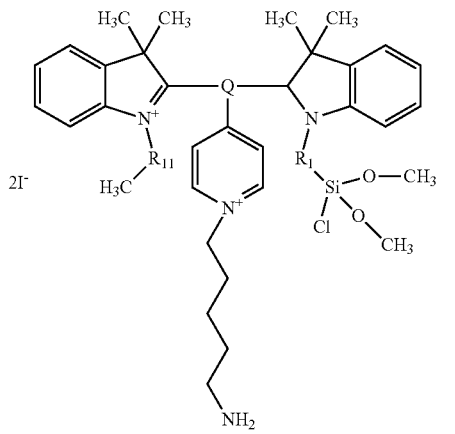

Formula I(t)
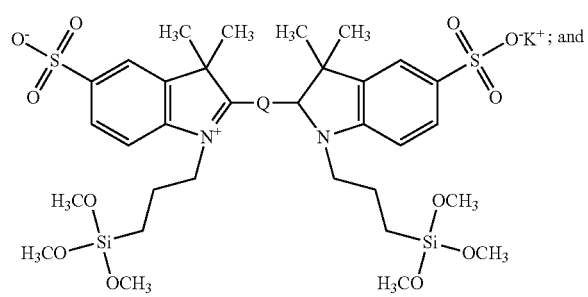

Formula I(u)
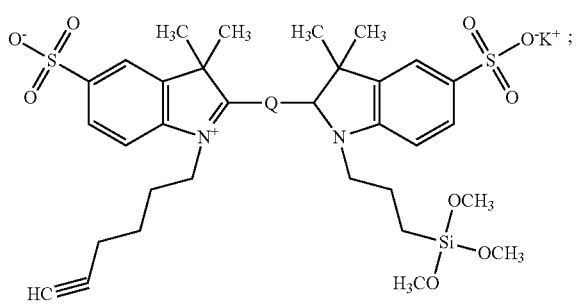

wherein $R_1$, $R_{11}$, $R_{21}$ and n have the meanings defined in claim 1.

4. A cyanine conjugated through a silane linker arm with a solid support having exposed hydroxyls, wherein the cyanine is a cyanine functionalized with a silane linker of formula (I), or a valence tautomer thereof:

Formula (I)
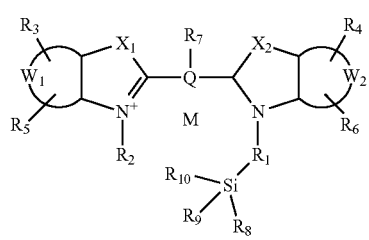

wherein:
$R_1$ is a linear, saturated or unsaturated alkyl chain, having 1 to 30 carbon atoms, wherein one or more carbon atoms are optionally substituted by a 4-, 5- or 6-membered aromatic or non aromatic cyclic grouping of carbon atoms;

$R_8$ and $R_9$ are independently selected from the group consisting of —$OCH_3$, —$OCH_2CH_3$, —$OCH_2CH_2CH_3$, —OCH(CH, —$OCH_2CH_2OCH_3$, —Cl, —Br, —I,

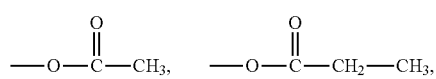

—$N(CH_3)_2$,

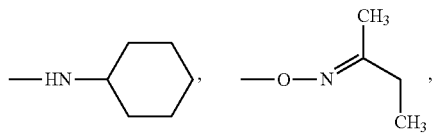

methyl, ethyl, propyl, and isopropyl;

$R_{10}$ is selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

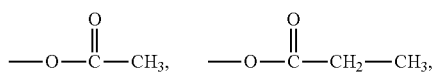

—$N(CH_2)_2$,

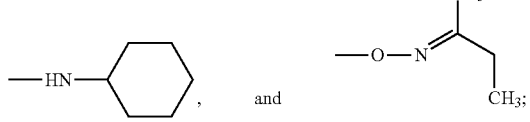

$W_1$ and $W_2$ are independently selected from a benzene ring or a naphthalene ring, in which one or more carbon atoms are optionally substituted by one or more heteroatoms selected from oxygen, sulfur, selenium and nitrogen, or one of $W_1$ and $W_2$ is absent, or both of $W_1$ and $W_2$ are absent;

$X_1$ and $X_2$ are independently selected from the group consisting of —O—, —S—, —Se—, —N—, —C(CH$_3$)$_2$, —CH=CH—, —NH—, and

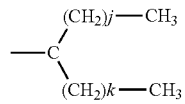

wherein j is an integer comprised between 1 and 20 and k is an integer comprised between 1 and 20;

$R_2$ is selected from the group consisting of hydrogen, —CH$_3$, and —R$_{11}$—Y$_1$, wherein R$_{11}$ is a linear, saturated or unsaturated alkyl chain, having 2 to 30 carbon atoms, wherein one or more carbon atoms are each substituted by a component independently selected from an oxygen atom, a sulfur atom, a —NH— group, a —CONH— group or a 4, 5 or 6-membered aromatic or non aromatic cyclic grouping of carbon atoms, wherein one or more carbon atoms are each optionally substituted by a heteroatom independently selected from oxygen, sulfur, nitrogen, or selenium, and wherein $Y_1$ is selected from the group consisting of hydrogen, methyl, carboxyl, carbonyl, amino, sulphydryl, thiocyanate, isothiocyanate, isocyanate, maleimide, hydroxyl, phosphoramidite, glycidyl, imidazolyl, carbamoyl, anhydride, bromoacetamido, chloroacetamido, iodoacetamido, sulphonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, azide, 3-(2-pyridyldithio)-propionamide, glyoxal, aldehyde, nitrophenyl, dinitrophenyl, trinitrophenyl, SO$_3$H, SO$_3^-$, —C≡CH and

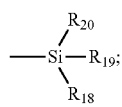

wherein $R_{18}$ and $R_{19}$ are independently selected from the group consisting of —OCH$_3$, —OCH$_2$CH$_3$, —OCH$_2$CH$_2$CH$_3$, —OCH(CH$_3$)$_2$, —OCH$_2$CH$_2$OCH$_3$, —Cl, —Br, —I,

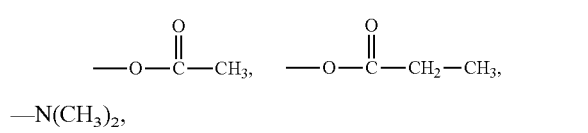

—N(CH$_3$)$_2$,

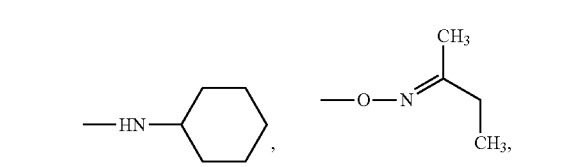

methyl, ethyl, propyl, and isopropyl;

$R_{20}$ is selected from the group consisting of —OCH$_3$, —OCH$_2$CH$_3$, —OCH$_2$CH$_2$CH$_3$, —OCH(CH$_3$)$_2$, —OCH$_2$CH$_2$OCH$_3$, —Cl, —Br, —I,

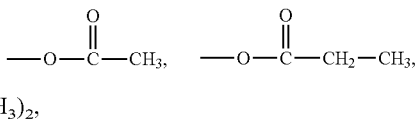

—N(CH$_3$)$_2$,

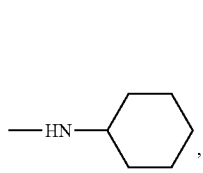 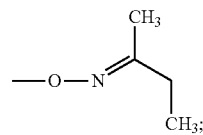

$R_3$, $R_4$, $R_5$ and $R_6$ are independently selected from the group consisting of hydrogen, —CH$_3$, —COOH, —OH, —NO$_9$, —OCH$_3$, —SO$_3$H, —SO$_3^-$, —Cl, —Br, —I, —O—(CH$_2$—CH$_2$—O)$_n$—CH$_3$ wherein n is an integer comprised between 1 and 100, and —R$_{21}$—Y$_2$, wherein R$_{21}$ is a linear, saturated or unsaturated alkyl chain having 2 to 30 carbon atoms, wherein one or more carbon atoms are each optionally substituted by a component independently selected from an oxygen atom, a sulfur atom, an —NH— group, —CONH group or a 4-, 5- or 6-membered aromatic or non aromatic cyclic grouping of carbon atoms, wherein one or more carbon atoms are each optionally substituted by a heteroatom independently selected from oxygen, sulfur, nitrogen, or selenium, and wherein $Y_2$ is selected from the group consisting of hydrogen, methyl, carboxyl, carbonyl, amino, sulphydryl, thiocyanate, isothiocyanate, isocyanate, maleimide, hydroxyl, phosphoramidite, glycidyl, imidazolyl, carbamoyl, anhydride, bromoacetamido, chloroacetamido, iodoacetamido, sulphonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, azide, 3-(2-pyridyldithio)-propionamide, glyoxal, aldehyde, nitrophenyl, dinitrophenyl, trinitrophenyl, —C≡CH, SO$_3$H, SO$_3^-$, and

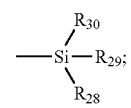

wherein $R_{28}$ and $R_{29}$ are independently selected from the group consisting of —OCH$_3$, —OCH$_2$CH$_3$, —OCH$_2$CH$_2$CH$_3$, —OCH(CH$_3$)$_2$, —OCH$_2$CH$_2$OCH$_3$, —Cl, —Br, —I,

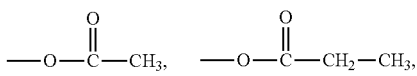

—N(CH$_3$)$_2$, 

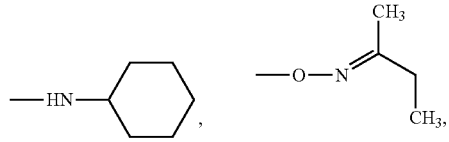

methyl, ethyl, propyl, and isopropyl;

$R_{30}$ is selected from the group consisting of —OCH$_3$, —OCH$_2$CH$_3$, —OCH$_2$CH$_2$CH$_3$, —OCH(CH$_3$)$_2$, —OCH$_2$CH$_2$OCH$_3$, —Cl, —Br, —I,

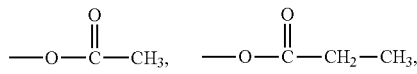

—N(CH$_3$)$_2$,

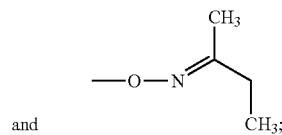

M is a counterion; and

Q is a polymethinic chain selected from the group consisting of:

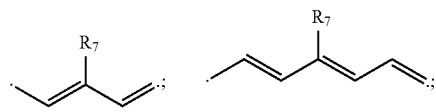

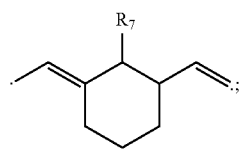

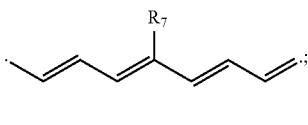

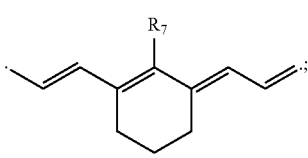

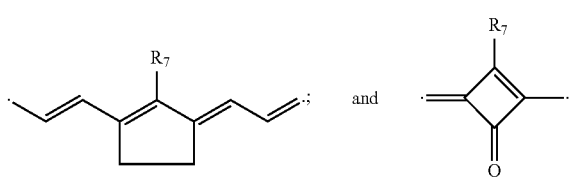

wherein $R_7$ is selected from the group consisting of hydrogen, halogen, =O, phenoxy, thiophenoxy, anilino, ciclohexylamino, piridine, —R$_{31}$—Y$_3$, —O—R$_{31}$—Y$_3$, —S—R$_{31}$—X$_3$, —NH—R$_{31}$—Y$_3$ and aryl optionally substituted with one or more substituents independently selected from the group consisting of —SO$_3$H, —SO$_3^-$, carboxyl (—COOH), amino (—NH), carbonyl (—CHO), thiocyanate (—SCN), isothiocyanate (—CNS), epoxy and —COZ wherein Z represents a leaving group, wherein $R_{31}$ has the same meanings as $R_{11}$ and $Y_3$ has the same meanings as $Y_1$.

5. The conjugated cyanine according to claim 4 wherein the cyanine is of formula (II), or a valence tautomer thereof:

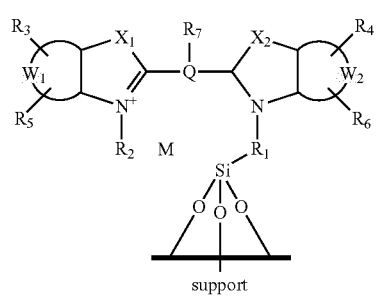

Formula (II)

wherein $R_1$, $R_2$, $R_3$, $R_4$, $R_5$, $R_6$, $R_7$, $X_1$, $X_2$, $W_1$, $W_2$, M and Q are as defined in claim 4.

6. The conjugated cyanine according to claim 4, wherein the cyanine is of general formula (III), or a valence tautomer thereof:

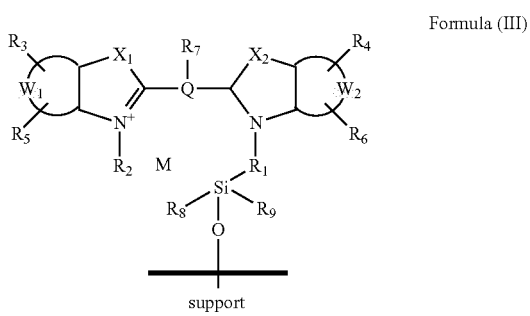

Formula (III)

wherein $R_1$, $R_2$, $R_3$, $R_4$, $R_5$, $R_6$, $R_7$, $X_1$, $X_2$, $W_1$, $W_2$, M and Q are as defined in claim 4.

7. The conjugated cyanine according to claim 4, wherein the solid support is a surface or a particle of any size and geometrical shape.

8. The conjugated cyanine according to claim 7, wherein the solid support is a nanoparticle.

9. The conjugated cyanine according to claim 4, wherein the solid support is selected from the group consisting of amorphous silica, zeolite, mesoporous silica, metal oxide, mixed oxide and inorganic semiconductor.

10. The cyanine according to claim 1, wherein at least one of $R_2$, $R_3$, $R_4$, $R_5$ and $R_6$ contains a reactive functional group different from a silane group.

11. The cyanine according to claim 10, wherein the reactive functional group different from the silane group is selected from carboxyl, amino, sulphydryl, thiocyanate, maleimide, succinimidyl ester, or hydrazine.

12. A cyanine, functionalized with a silane linker of formula (I), or a valence tautomer thereof:

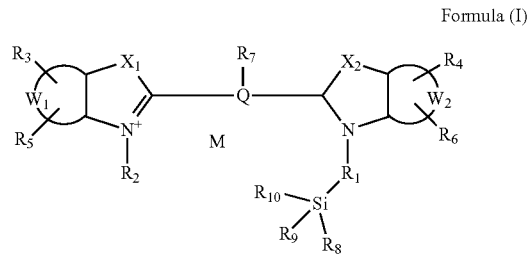

Formula (I)

wherein:

$R_1$ is a linear, saturated or unsaturated alkyl chain, having 1 to 30 carbon atoms, wherein one or more carbon atoms are optionally substituted by a 4-, 5- or 6-membered aromatic or non aromatic cyclic grouping of carbon atoms;

$R_8$ and $R_9$ are independently selected from the group consisting of —OCH$_3$, —OCH$_2$CH$_3$, —OCH$_2$CH$_2$CH$_3$, —OCH(CH$_3$)$_2$, —OCH$_2$CH$_2$OCH$_3$, —Cl, —Br, —I,

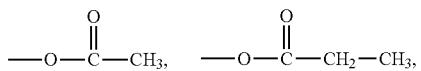

—N(CH$_3$)$_2$,

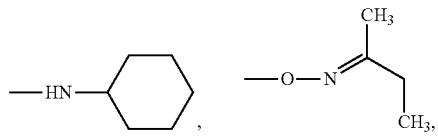

methyl, ethyl, propyl, and isopropyl;

$R_{10}$ is selected from the group consisting of —OCH$_3$, —OCH$_2$CH$_3$, —OCH$_2$CH$_7$CH$_3$, —OCH(CH$_3$)$_2$, —OCH$_2$CH$_2$OCH$_3$, —Cl, —Br, —I,

—N(CH$_3$)$_2$,

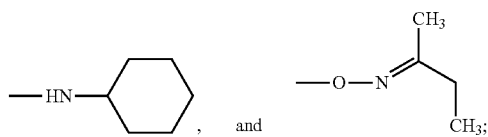

$W_1$ and $W_2$ are independently selected from a benzene ring or a naphthalene ring, in which one or more carbon atoms are optionally substituted by one or more heteroatoms selected from oxygen, sulfur, selenium and nitrogen, or one of $W_1$ and $W_2$ is absent, or both of $W_1$ and $W_2$ are absent;

$X_1$ and $X_2$ are independently selected from the group consisting of —O—, —S—, —Se—, —N—, —C(CH$_3$)$_2$, —CH=CH—, —NH—, and

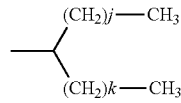

wherein j is an integer comprised between 1 and 20 and k is an integer comprised between 1 and 20;

$R_2$ is selected from the group consisting of hydrogen, —CH$_3$, and —R$_{11}$—Y$_1$, wherein $R_{11}$ is a linear, saturated or unsaturated alkyl chain, having 2 to 30 carbon atoms, wherein one or more carbon atoms are each substituted by a component independently selected from an oxygen atom, a sulfur atom, a —NH— group, a —CONH— group or a 4, 5 or 6-membered aromatic or non aromatic cyclic grouping of carbon atoms, wherein one or more carbon atoms are each optionally substituted by a heteroatom independently selected from oxygen, sulfur, nitrogen, or selenium, and wherein $Y_1$ is selected from the group consisting of hydrogen, methyl, carboxyl, carbonyl, amino, sulphydryl, thiocyanate, isothiocyanate, isocyanate, maleimide, hydroxyl, phosphoramidite, glycidyl, imidazolyl, carbamoyl, anhydride, bromoacetamido, chloroacetamido, iodoacetamido, sulphonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, wide, 3-(2-pyridyldithio)-propionamide, glyoxal, aldehyde, nitrophenyl, dinitrophenyl, trinitrophenyl, SO$_3$H, SO$_3^-$, —C≡CH and

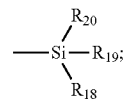

wherein $R_{18}$ and $R_{19}$ are independently selected from the group consisting of —OCH$_3$, —OCH$_2$CH$_3$, —OCH$_2$CH$_2$CH$_3$, —OCH(CH$_3$)$_2$, —OCH$_2$CH$_2$OCH$_3$, —Cl, —Br, —I,

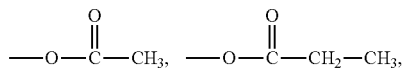

—N(CH$_3$)$_2$,

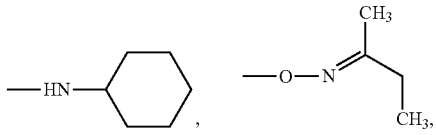

methyl, ethyl, propyl, and isopropyl;

$R_{20}$ is selected from the group consisting of —OCH$_3$, —OCH$_2$CH$_3$, —OCH$_2$CH$_2$CH$_3$, —OCH(CH$_3$)$_2$, —OCH$_2$CH$_2$OCH$_3$, —Cl, —Br, —I,

—N(CH$_3$)$_2$,

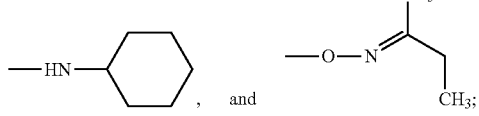

$R_3$, $R_4$, $R_5$ and $R_6$ are independently selected from the group consisting of hydrogen, —CH$_3$, —COOH, —OH, —NO$_2$, —OCH$_3$, —SO$_3$H, —SO$_3^-$, —Cl, —Br, —I, —O—(CH$_2$—CH$_2$—O)$_n$—CH$_3$ wherein n is an integer comprised between 1 and 100, and —R$_{21}$—Y$_2$, wherein $R_{21}$ is a linear, saturated or unsaturated alkyl chain having 2 to 30 carbon atoms, wherein one or more carbon atoms are each optionally substituted by a component independently selected from an oxygen atom, a sulfur atom, an —NH— group, —CONH group or a 4-, 5- or 6-membered aromatic or non aromatic cyclic grouping of carbon atoms, wherein one or more carbon atoms are each optionally substituted by a heteroatom independently selected from oxygen, sulfur, nitrogen, or selenium, and wherein $Y_2$ is selected from the group consisting of hydrogen, methyl, carboxyl, carbonyl, amino, sulphydryl, thiocyanate, isothiocyanate, isocyanate, maleimide, hydroxyl, phosphoramidite, glycidyl, imidazolyl, carbamoyl, anhydride, bromoacetamido, chloroacetamido, iodoacetamido, sulphonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, azide, 3-(2-pyridyldithio)-propionamide, glyoxal, aldehyde, nitrophenyl, dinitrophenyl, trinitrophenyl, —C≡CH, $SO_3H$, $SO_3^-$, and $$-Si\begin{pmatrix}R_{30}\\R_{29}\\R_{28}\end{pmatrix};$$

wherein $R_{28}$ and $R_{29}$ are independently selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

—O—C(=O)—$CH_3$, —O—C(=O)—$CH_2$—$CH_3$,

—N($CH_3$)$_2$,

—HN—cyclohexyl, —O—N=C($CH_3$)—$CH_2$—$CH_3$, methyl, ethyl, propyl, and isopropyl;

$R_{30}$ is selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

—O—C(=O)—$CH_3$, —O—C(=O)—$CH_2$—$CH_3$,

—N($CH_3$)$_2$,

—HN—cyclohexyl, and —O—N=C($CH_3$)—$CH_2$—$CH_3$;

M is a counterion; and

Q is a polymethinic chain selected from the group consisting of:

[structures with $R_7$ substituents]

wherein $R_7$ is selected from the group consisting of hydrogen, halogen, phenoxy, thiophenoxy, anilino, ciclohexylamino, piridine, —$R_{31}$—$Y_3$, —O—$R_{31}$—$Y_3$, —S—$R_{31}$—$Y_3$, —NH—$R_{31}$—$Y_3$ and aryl optionally substituted with one or more substituents independently selected from the group consisting of —$SO_3H$, —$SO_3^-$, carboxyl (—COOH), amino (—$NH_2$), carbonyl (—CHO), thiocyanate (—SCN), isothiocyanate (—CNS), epoxy and —COZ wherein Z represents a leaving group, wherein $R_{31}$ has the same meanings as $R_{11}$ and $Y_3$ has the same meanings as $Y_1$, and wherein at least one of $R_2$, $R_3$, $R_4$, $R_5$ and $R_6$ contains a reactive functional group different from a silane group and the cyanine is conjugated with a biomolecule through the reactive functional group different from a silane group.

13. A cyanine conjugated through a silane linker arm with a solid support having exposed hydroxyls, wherein the cyanine is a cyanine functionalized with a silane linker of formula (I), or a valence tautomer thereof:

Formula (I)

[structure of Formula (I) with substituents $R_1$–$R_{10}$, $W_1$, $W_2$, $X_1$, $X_2$, M, Q]

wherein:

$R_1$ is a linear, saturated or unsaturated alkyl chain, having 1 to 30 carbon atoms, wherein one or more carbon atoms are optionally substituted by a 4-, 5- or 6-membered aromatic or non aromatic cyclic grouping of carbon atoms;

$R_8$ and $R_9$ are independently selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

—O—C(=O)—$CH_3$, —O—C(=O)—$CH_2$—$CH_3$,

—N($CH_3$)$_2$,

—HN—cyclohexyl, —O—N=C($CH_3$)—$CH_2$—$CH_3$, methyl, ethyl, propyl, and isopropyl, $R_{10}$ is selected from the group consisting of —$OCH_3$, —$OCH_2CH_3$, —$OCH_2CH_2CH_3$, —$OCH(CH_3)_2$, —$OCH_2CH_2OCH_3$, —Cl, —Br, —I,

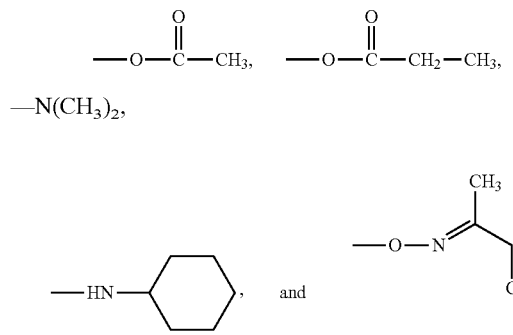

W₁ and W₂ are independently selected from a benzene ring or a naphthalene ring, in which one or more carbon atoms are optionally substituted by one or more heteroatoms selected from oxygen, sulfur, selenium and nitrogen, or one of W₁ and W₂ is absent, or both of W₁ and W₂ are absent;

X₁ and X₂ are independently selected from the group consisting of —O—, —S—, —Se—, —N—, —C(CH₃)₂, —CH=CH—, —NH—, and

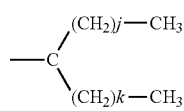

wherein j is an integer comprised between 1 and 20 and k is an integer comprised between 1 and 20;

R2 is selected from the group consisting of hydrogen, —CH₃ and —R₁₁—Y₁, wherein R₁₁ is a linear, saturated or unsaturated alkyl chain, having 2 to 30 carbon atoms, wherein one or more carbon atoms are each substituted by a component independently selected from an oxygen atom, a sulfur atom, a —NH— group, a —CONH— group or a 4, 5 or 6-membered aromatic or non aromatic cyclic grouping of carbon atoms, wherein one or more carbon atoms are each optionally substituted by a heteroatom independently selected from oxygen, sulfur, nitrogen, or selenium, and wherein Y₁ is selected from the group consisting of hydrogen, methyl, carboxyl, carbonyl, amino, sulphydryl, thiocyanate, isothiocyanate, isocyanate, maleimide, hydroxyl, phosphoramidite, glycidyl, imidazolyl, carbamoyl, anhydride, bromoacetamido, chloroacetamido, iodoacetamido, sulphonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, azide, 3-(2-nyridyldithio)-propionamide, glyoxal, aldehyde, nitrophenyl, dinitrophenyl, trinitrophenyl, SO₃H, SO₃⁻, —C≡CH and

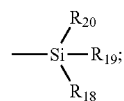

wherein R₁₈ and R₁₉ are independently selected from the group consisting of —OCH₃, —OCH₂CH₃, —OCH₂CH₂CH₃, —OCH(CH₃)₂, —OCH₂CH₂OCH₃, —Cl, —Br, —I,

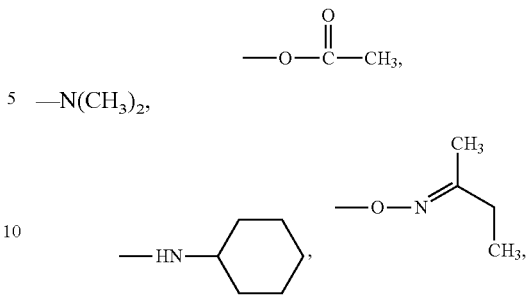

methyl, ethyl, propyl, and isopropyl;

R₂₀ is selected from the group consisting of —OCH₃, —OCH₂CH₃, —OCH₂CH₂CH₃—OCH(CH₃)₂, —OCH₂CH₂OCH₃, —Cl, —Br, —I,

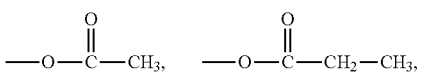

—N(CH₃)₂,

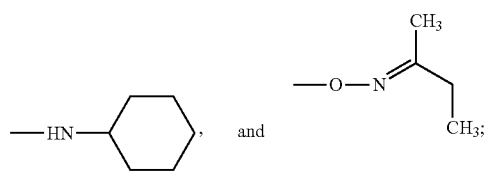

R₃, R₄, R₅ and R₆ are independently selected from the group consisting of hydrogen, —CH₃, —COOH, —OH, —NO₇, —OCH₃, —SO₃H, —SO₃⁻, —Cl, —Br, —I, —O—(CH₂—CH₂—O)ₙ—CH₃ wherein n is an integer comprised between 1 and 100, and —R₂₁—Y₇, wherein R₂₁ is a linear, saturated or unsaturated alkyl chain having 2 to 30 carbon atoms, wherein one or more carbon atoms are each optionally substituted by a component independently selected from an oxygen atom, a sulfur atom, an —NH— group, —CONH group or a 4-, 5- or 6-membered aromatic or non aromatic cyclic grouping of carbon atoms, wherein one or more carbon atoms are each optionally substituted by a heteroatom independently selected from oxygen, sulfur, nitrogen, or selenium, and wherein Y₂ is selected from the group consisting of hydrogen, methyl, carboxyl, carbonyl, amino, sulphydryl, thiocyanate, isothiocyanate, isocyanate, maleimide, hydroxyl, phosphoramidite, glycidyl, imidazolyl, carbamoyl, anhydride, bromoacetamido, chloroacetamido, iodoacetamido, sulphonyl halide, acyl halide, aryl halide, hydrazide, succinimidyl ester, hydroxysulfosuccinimidyl ester, phthalimidyl ester, naphthalimidyl ester, monochlorotriazine, dichlorotriazine, mono- or di-halide substituted pyridine, mono- or di-halide substituted diazine, aziridine, imidic ester, hydrazine, azidonitrophenyl, azide, 3-(2-pyridyldithio)-propionamide, glyoxal, aldehyde, nitrophenyl, dinitrophenyl, trinitrophenyl, —C≡CH, SO₃H, SO₃⁻, and

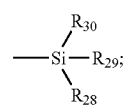

wherein R₂₈ and R₂₉ are independently selected from the group consisting of —OCH₃, —OCH₂CH₃, —OCH₂CH₂CH₃, —OCH(CH₃)₂, —OCH₂CH₂OCH₃, —Cl, —Br, —I,

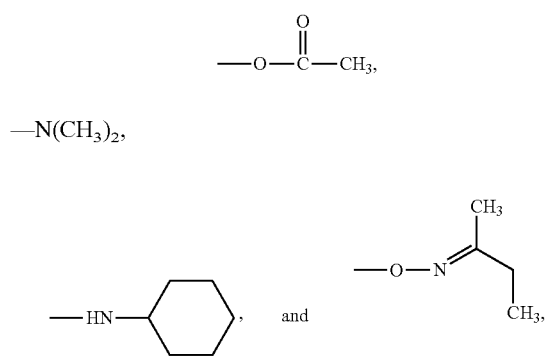

methyl, ethyl, propyl, and isopropyl;

$R_{30}$ is selected from the group consisting of —OCH$_3$, —OCH$_2$CH$_3$, —OCH$_2$CH$_2$CH$_3$, —OCH(CH$_3$)$_2$, —OCH$_2$CH$_2$OCH$_3$, —Cl, —Br, —I,

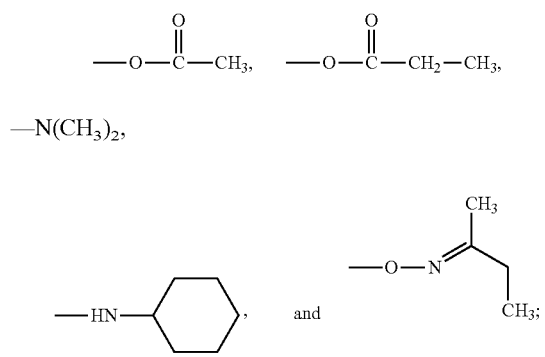

M is a counterion; and

Q is a polymethinic chain selected from the group consisting of:

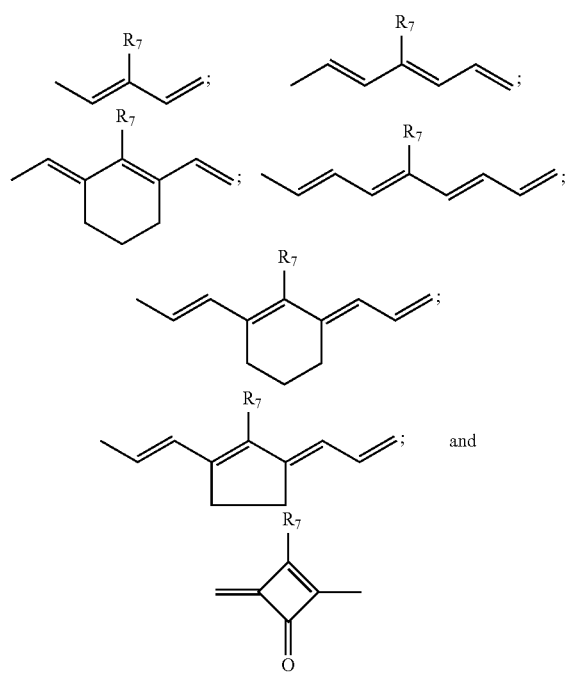

wherein $R_7$ is selected from the group consisting of hydrogen, halogen, =O, phenoxy, thiophenoxy, anilino, ciclohexylamino, piridine, —R$_{31}$—Y$_3$, —O—R$_{31}$—Y$_3$, —S—R$_{31}$—Y$_3$, —NH—R$_{31}$—Y$_3$ and aryl optionally substituted with one or more substituents independently selected from the group consisting of —SO$_3$H, —SO$_3^-$, carboxyl (—COOH), amino (—NH$_2$), carbonyl (—CHO), thiocyanate (—SCN), isothiocyanate (—CNS), epoxy and —COZ wherein Z represents a leaving group, wherein $R_{31}$ has the same meanings as $R_{11}$ and $Y_3$ has the same meanings as $Y_1$, and wherein at least one of $R_2$, $R_3$, $R_4$, $R_5$ and $R_6$ contains a reactive functional group different from a silane group and the cyanine is conjugated with a biomolecule through the reactive functional group different from a silane group.

14. The cyanine according to claim 13 of the formula (IV), or a valence tautomer thereof:

Formula (IV)

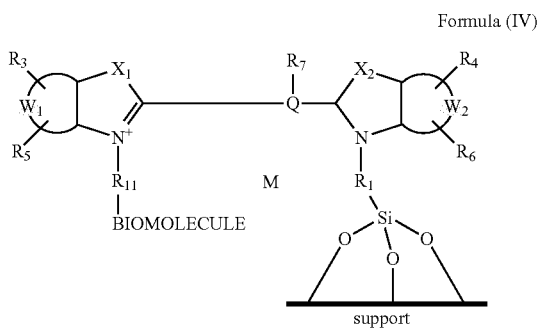

wherein $R_1$, $R_3$, $R_4$, $R_5$, $R_6$, $R_7$, $R_{11}$, $X_1$, $X_2$, $W_1$, $W_2$, M and Q have the meanings as defined in claim 13.

15. The cyanine according to claim 13, having the general formula (V), or a valence tautomer thereof:

Formula (V)

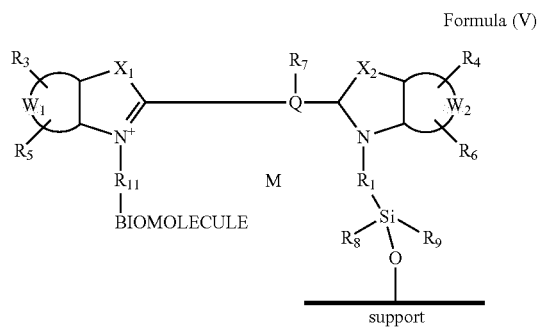

wherein $R_1$, $R_3$, $R_4$, $R_5$, $R_6$, $R_7$, $R_{11}$, $X_1$, $X_2$, $W_1$, $W_2$, M and Q have the meanings as defined in claim 13.

16. The cyanine according to claim 12, wherein the biomolecule is selected from the group consisting of nucleosides, nucleotides, DNA, RNA, PNA, antibodies, proteins, peptides, hormones and vitamins.

* * * * *